(12) United States Patent
Nakatani et al.

(10) Patent No.: US 8,318,477 B2
(45) Date of Patent: Nov. 27, 2012

(54) CELLULAR ELECTROPHYSIOLOGICAL MEASUREMENT DEVICE AND METHOD FOR MANUFACTURING THE SAME

(75) Inventors: Masaya Nakatani, Osaka (JP); Takashi Yoshida, Kyoto (JP); Masatoshi Kojima, Kyoto (JP)

(73) Assignee: Panasonic Corporation, Osaka (JP)

( * ) Notice: Subject to any disclaimer, the term of this patent is extended or adjusted under 35 U.S.C. 154(b) by 1310 days.

(21) Appl. No.: 11/915,172

(22) PCT Filed: May 31, 2006

(86) PCT No.: PCT/JP2006/310846
§ 371 (c)(1),
(2), (4) Date: Nov. 21, 2007

(87) PCT Pub. No.: WO2006/132116
PCT Pub. Date: Dec. 14, 2006

(65) Prior Publication Data
US 2009/0047731 A1    Feb. 19, 2009

(30) Foreign Application Priority Data
Jun. 7, 2005  (JP) .................................. 2005-166492

(51) Int. Cl.
*C12M 1/34* (2006.01)
*C23F 1/00* (2006.01)

(52) U.S. Cl. ................ 435/288.3; 204/400; 204/403.01; 205/777.5; 205/778; 435/285.2; 216/11; 216/38; 216/39; 216/41; 422/82.01

(58) Field of Classification Search .............. 435/288.3, 435/287.1; 204/400, 403.1; 205/777.5, 778; 216/11, 38, 39, 41; 422/82.01
See application file for complete search history.

(56) References Cited

U.S. PATENT DOCUMENTS

| 5,183,744 | A | | 2/1993 | Kawamura et al. |
| 5,614,935 | A | * | 3/1997 | Ogi et al. ................. 347/213 |
| 6,146,740 | A | * | 11/2000 | Birukawa et al. ............ 428/141 |
| 6,593,241 | B1 | * | 7/2003 | Abraham et al. ............ 438/697 |
| 6,682,649 | B1 | | 1/2004 | Petersen et al. |
| 6,758,961 | B1 | | 7/2004 | Vogel et al. |

(Continued)

FOREIGN PATENT DOCUMENTS
CN        1458972 A        11/2003
(Continued)

OTHER PUBLICATIONS

JP OA for Application No. 2008-310641, Jan. 28, 2011, Panasonic Corp.

(Continued)

*Primary Examiner* — William H Beisner
*Assistant Examiner* — Danielle Henkel
(74) *Attorney, Agent, or Firm* — RatnerPrestia

(57) ABSTRACT

A cellular electrophysiological measurement device includes a thin plate and a frame. The thin plate has a first surface with a depression and a second surface with a through-hole. The frame is in contact with an outer periphery on the second surface of thin plate. The thin plate has a laminated structure of at least two layers including a first material layer on the first surface and a second material layer on the second surface. The frame is formed of a third material layer. The structure allows the cellular electrophysiological measurement device to be not so vulnerable to breakage of thin plate and other damages, thereby having high production yield.

17 Claims, 23 Drawing Sheets

U.S. PATENT DOCUMENTS

| | | | |
|---|---|---|---|
| 6,984,297 | B2 | 1/2006 | Nisch et al. |
| 7,006,929 | B2 | 2/2006 | Oka et al. |
| 2001/0046706 | A1 | 11/2001 | Rubinsky |
| 2002/0074227 | A1 | 6/2002 | Nisch |
| 2002/0104757 | A1 | 8/2002 | Schmidt |
| 2002/0144905 | A1 | 10/2002 | Schmidt |
| 2003/0025200 | A1* | 2/2003 | Katsumura et al. ........... 257/734 |
| 2003/0052002 | A1 | 3/2003 | Vogel et al. |
| 2003/0107386 | A1* | 6/2003 | Dodgson et al. .............. 324/699 |
| 2003/0113833 | A1* | 6/2003 | Oka et al. ........................ 435/29 |
| 2004/0033483 | A1 | 2/2004 | Oka et al. |
| 2004/0055901 | A1 | 3/2004 | Petersen et al. |
| 2004/0197898 | A1* | 10/2004 | Nakatani et al. ........... 435/287.1 |
| 2005/0112756 | A1 | 5/2005 | Nakatani et al. |
| 2005/0214740 | A1 | 9/2005 | Ushio et al. |
| 2005/0221469 | A1 | 10/2005 | Nakatani et al. |
| 2006/0163063 | A1 | 7/2006 | Picollet-Dahan |
| 2008/0257726 | A1 | 10/2008 | Nakatani et al. |

FOREIGN PATENT DOCUMENTS

| | | |
|---|---|---|
| EP | 0 652 308 B1 | 3/2002 |
| FR | 2844052 A1 | 3/2004 |
| JP | 2-131569 | 5/1990 |
| JP | 06-244257 A | 9/1994 |
| JP | 2003-511668 A | 3/2003 |
| JP | 2003-511699 A | 3/2003 |
| JP | 2004-271330 A | 9/2004 |
| JP | 2004-271331 A | 9/2004 |
| JP | 2005-156234 A | 6/2005 |
| JP | 2005-265758 A | 9/2005 |
| WO | WO 99/31503 | 6/1999 |
| WO | WO 02/055653 A1 | 7/2002 |
| WO | WO 02/099408 A1 | 12/2002 |
| WO | WO 03/016555 A1 | 2/2003 |
| WO | WO-2004038410 A1 | 5/2004 |

OTHER PUBLICATIONS

International Search Report for Application No. PCT/JP2006/310846, filed Sep. 19, 2006.

Japanese Office Action for Application No. 2010-186807, Mar. 29, 2011, Panasonic Corporation.

European Application Serial No. 05765636.5, Extended European Search Report mailed Jan. 30, 2012, 5 pgs.

* cited by examiner

CELLULAR ELECTROPHYSIOLOGICAL MEASUREMENT DEVICE AND METHOD FOR MANUFACTURING THE SAME

This application is a U.S. national phase application of PCT international application PCT/JP2006/310846, filed May 31, 2006.

TECHNICAL FIELD

The present invention relates to a cellular electrophysiological measurement device used to measure the potentials inside and outside a cell or physicochemical changes in a cell due to cellular activities, and also relates to a method for manufacturing the device. The device and method can be used in drug screening to detect a reaction of a cell to a chemical substance or other stimulus.

BACKGROUND ART

The following is a conventional method for measuring the potentials inside and outside a cell (hereinafter, cellular potentials) or other cellular electrophysiological phenomena caused by cellular electrophysiological activities.

As a conventional cellular electrophysiological measurement device, it is known to measure cellular potentials by using a substrate having a cell holding means and an electrode provided on the cell holding means. In this cellular electrophysiological measurement device, the cell holding means captures a cell and places the cell in such a manner as to separate the space in the device into two regions. The separated two regions provide a potential difference therebetween, and the potential difference can be measured to determine changes in the cellular potential. One such type of cellular electrophysiological measurement device is disclosed in International Publication No. WO02/055653.

FIG. 19 is a sectional view showing the aforementioned conventional cellular electrophysiological measurement device. Cellular electrophysiological measurement device 130 (hereinafter, device 130) includes well 120 with measuring solution 121A and substrate 123 provided with cell holder 131 (hereinafter, holder 131) for capturing and holding cell 122. Holder 131 is formed of depression 124, opening 125, and through-hole 126 connected to depression 124 through opening 125. Depression 124, opening 125, and through-hole 126 are formed in substrate 123.

The space of device 130 with the aforementioned structured is separated by cell 122 into two regions. One region contains measuring solution 121A provided with reference electrode 127 and the other region contains measuring solution 121B provided with measuring electrode 128. Measuring electrode 128 outputs the potential of measuring solution 121B contained in through-hole 126 through wiring.

When the potentials inside and outside the cell are measured with device 130, cell 122 is sucked by such as a suction pump (unillustrated) from the through-hole 126 side, thereby being tightly held on the opening of depression 124. Then, the electrical signal generated when cell 122 is activated is detected with measuring electrode 128.

SUMMARY OF THE INVENTION

An object of the present invention is to provide a cellular electrophysiological measurement device with a substrate that is not easily broken in spite of its thinness so as to perform high precision measurement of cellular electrophysiological phenomena.

The cellular electrophysiological measurement device of the present invention includes a thin plate and a frame. The thin plate has a first surface with a depression and a second surface with a through-hole. The frame is in contact with an outer periphery on the second surface of the thin plate. The thin plate has a laminated structure of at least two layers including a first material layer on the first surface and a second material layer on the second surface. The frame is formed of a third material layer. This structure allows the cellular electrophysiological measurement device to be not so vulnerable to breakage of the thin plate and other damages, thereby having high production yield.

A method of the present invention for manufacturing a cellular electrophysiological measurement device is a method for manufacturing a cellular electrophysiological measurement device which measures a cellular electrophysiological activity and includes the following components: a thin plate having a first surface and a second surface; a depression provided on the first surface of the thin plate; a through-hole provided on the second surface of the thin plate; and a frame in contact with the second surface of the thin plate. The method includes the following steps: a substrate preparation step for preparing a substrate having a laminated structure consisting of a first material layer, a second material layer, and a third material layer; a first-resist-film forming step for forming a first etching resist film having a first resist film opening on a side of the first material layer of the substrate; a depression forming step for forming the depression in the first material layer by introducing a first etching gas from the first resist film opening; a first through-hole forming step for forming a first hole in the first material layer by introducing a second etching gas and a third etching gas from the first resist film opening; a first-resist-film removing step for removing the first etching resist film; a second through-hole forming step for forming a second hole in the second material layer by introducing a fourth etching gas; a second-resist-film forming step for forming a second etching resist film having a second resist film opening on a side of the third material layer of the substrate; and a frame forming step for forming the frame by introducing the second etching gas and the third etching gas from the second resist film opening. This method can provide a cellular electrophysiological measurement device which is not so vulnerable to breakage of the thin plate and other damages, and this method has high productivity to manufacture the cellular electrophysiological measurement device.

Figure 1:
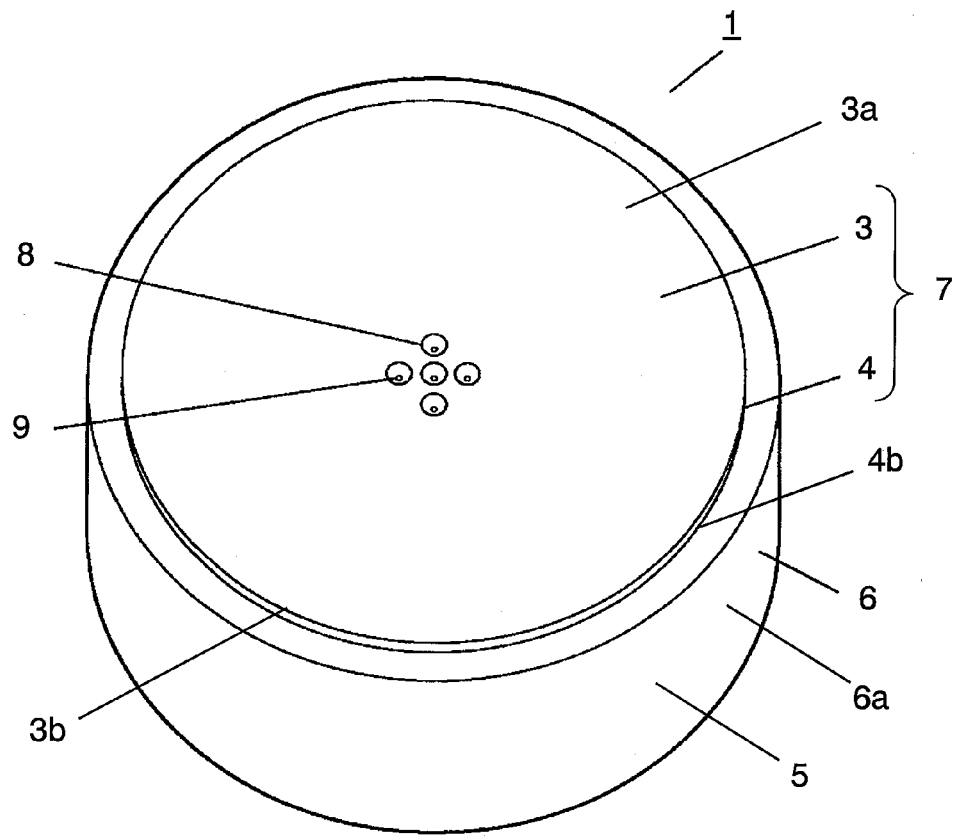
FIG. 1 is a perspective view of a cellular electrophysiological measurement device of a first embodiment of the present invention.

REFERENCE MARKS IN THE DRAWINGS 1, 1a, 1b, 1c, 1d, 1e, 1f, 1g, 1h, 1j, 1k, 1m, 1n, 1p cellular electrophysiological measurement device
2 substrate
3 first material layer
3a first surface
3b upper outer peripheral edge
4 second material layer
4a second surface
4b outer periphery of thin plate
5 third material layer
6 frame
6a outer periphery of frame 6b inner wall
6c outer peripheral edge
6d inner wall edge
6e lower edge
6f top edge
7 thin plate
8 depression
8a first opening
8b bottom
9 through-hole
9a first hole
9b second hole
9c second opening
9d third opening
9e inner wall
9f protective film
9g, 9h edge
9j protective layer
10 vessel
10a upper part of vessel
10b lower part of vessel
11 partition
12 cavity
13 reference electrode
14 measuring electrode
15a, 15b measuring solution
16 cell
17 first etching resist film
17a first resist opening
18 second etching resist film
18a second resist opening
21, 21a cellular potential measuring apparatus
22 protrusion
23 recess

DETAILED DESCRIPTION OF PREFERRED EMBODIMENTS

First Exemplary Embodiment

A cellular electrophysiological measurement device of a first embodiment and a method for manufacturing the device will be described as follows with reference to drawings.

Figure 2:
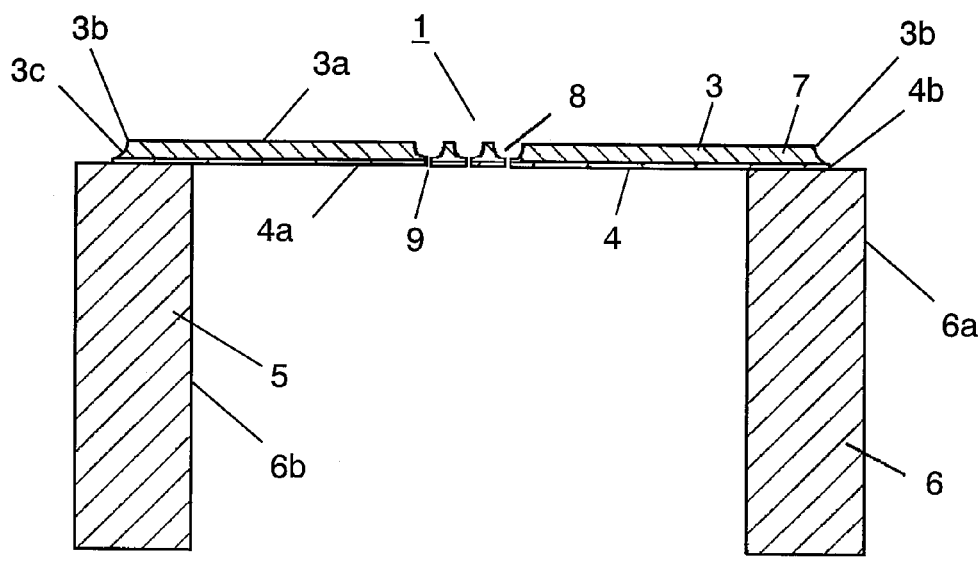
FIG. 2 is a sectional view of the cellular electrophysiological measurement device shown in FIG. 1.
Figure 3:
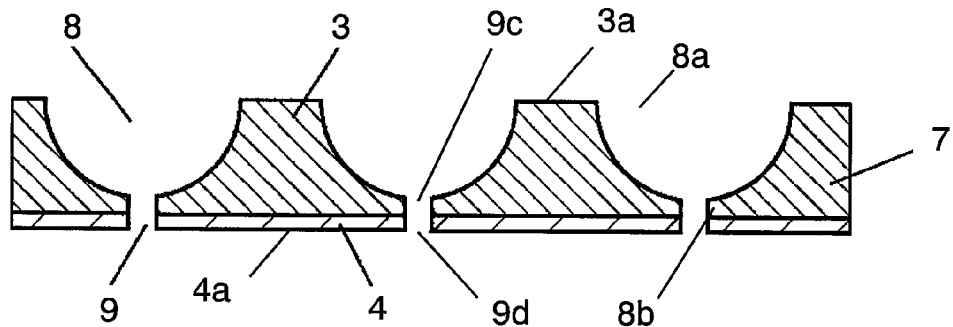
FIG. 3 is an enlarged sectional view of an essential part of the cellular electrophysiological measurement device shown in FIG. 1.
Figure 4:
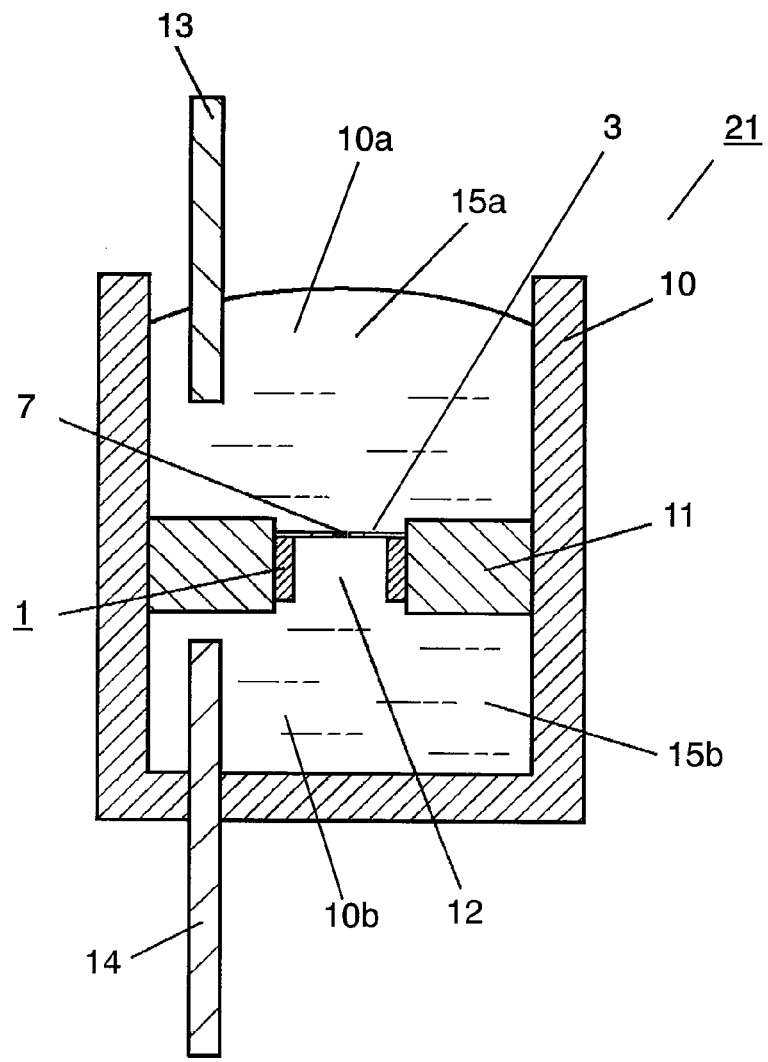
FIG. 4 is a schematic sectional view of a cellular potential measuring apparatus in which the cellular electrophysiological measurement device shown in FIG. 1 has been placed.

FIG. 1 is a perspective view of the cellular electrophysiological measurement device of the first embodiment. FIG. 2 is a sectional view of the device shown in FIG. 1. FIG. 3 is an enlarged sectional view of an essential part of the device shown in FIG. 1. FIG. 4 is a schematic sectional view of a cellular potential measuring apparatus.

In FIGS. 1 to 3, cellular electrophysiological measurement device 1 (hereinafter, device 1) of the first embodiment is featured by thin plate 7 formed of at least two laminated layers made of a different material from each other. First surface 3a side of thin plate 7 is constructed from first material layer 3 (hereinafter, layer 3) made of silicon, and second surface 4a side of thin plate 7 is constructed from second material layer 4 (hereinafter, layer 4) made of silicon dioxide. On the side of second surface 4a, outer periphery 4b of thin plate (hereinafter, outer periphery 4b) is in contact with frame 6 formed of third material layer 5 (hereinafter, layer 5) made of silicon. Second surface 4a is a flat surface.

Inside thin plate 7, layer 3 has at least one depression 8 with first opening 8a (hereinafter, opening 8a) on the side of first surface 3a. Depression 8 is connected to through-hole 9 which is formed beneath depression 8 in such a manner as to extend between second opening 9c (hereinafter, opening 9c) and third opening 9d (hereinafter, opening 9d). Through-hole 9 is formed on both layer 3 and layer 4. Opening 9d is disposed on the side of second surface 4a.

As shown in FIG. 2, layer 3 has upper outer peripheral edge 3b (hereinafter, edge 3b) provided with rounded part 3c.

The following is a brief description of a method for measuring cellular electrophysiological activity using device 1. FIG. 4 is a schematic sectional view of the measuring apparatus in which the cellular electrophysiological measurement device shown in FIG. 1 has been placed.

As shown in FIG. 4, first of all, device 1 is installed inside partition 11. Partition 11 with cavity 12 is provided in vessel 10 made of plastic or other insulating material. Device 1 is tight fit in cavity 12 with layer 3 up so as to separate a space in vessel 10 into two regions by partition 11. The upper and lower regions of vessel 10 separated by partition 11 contain measuring solution 15a (hereinafter, solution 15a) and measuring solution 15b (hereinafter, solution 15b), respectively. Vessel 10 is separated to upper part 10a of vessel (hereinafter, upper part 10a) and lower part 10b of vessel (hereinafter, lower part 10b). Solution 15a contained in upper part 10a of vessel 10 is provided with reference electrode 13 (hereinafter, electrode 13) formed of a silver-silver chloride electrode or the like. Solution 15b contained in lower part 10b of vessel 10 is provided with measuring electrode 14 (hereinafter, electrode 14) formed of a silver-silver chloride electrode or the like. Note that electrode 13 and electrode 14 can be replaced by each other. Cellular potential measuring apparatus 21 (hereinafter, apparatus 21) is structured in this manner.

Figure 5:
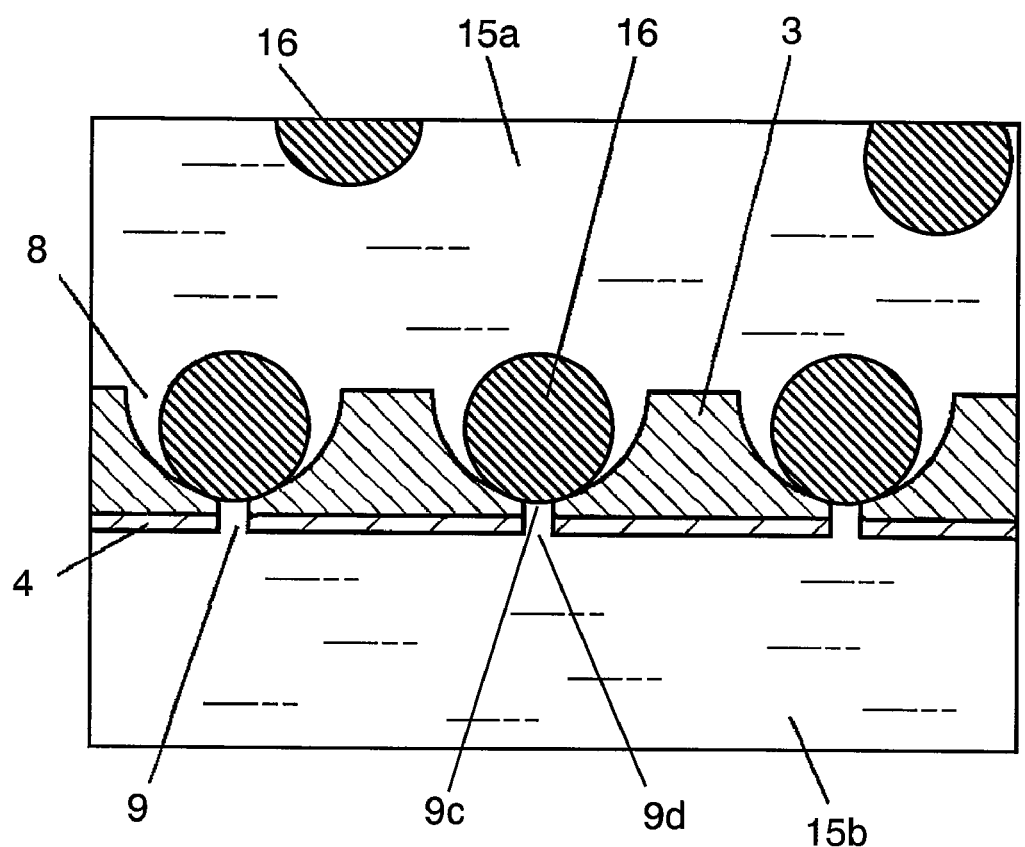
FIG. 5 is an enlarged sectional view of an essential part of the cellular potential measuring apparatus shown in FIG. 4.

Next, after preparing apparatus 21, cell 16 as a measurement target is placed into vessel 10 from a side of upper part 10a. Cell 16 placed in vessel 10 is then sucked with a suction pump (unillustrated) or the like, so as to make lower part 10b lower in pressure than upper part 10a and to have a predetermined pressure difference between the upper and lower of partition 11. This allows cell 16 to be sucked and held on opening 9c as shown in FIG. 5. When this pressure difference is maintained, an adhesion of cell 16 to opening 9c is secured, thereby allowing solutions 15a and 15b to have an electrical resistance therebetween. When subjected to a stimulus such as a drug or other chemical compound, cell 16 shows an electrophysiological response. As a result, an electrical response or change in terms of voltage, current, or other parameters is observed between electrodes 13 and 14.

Figure 6:
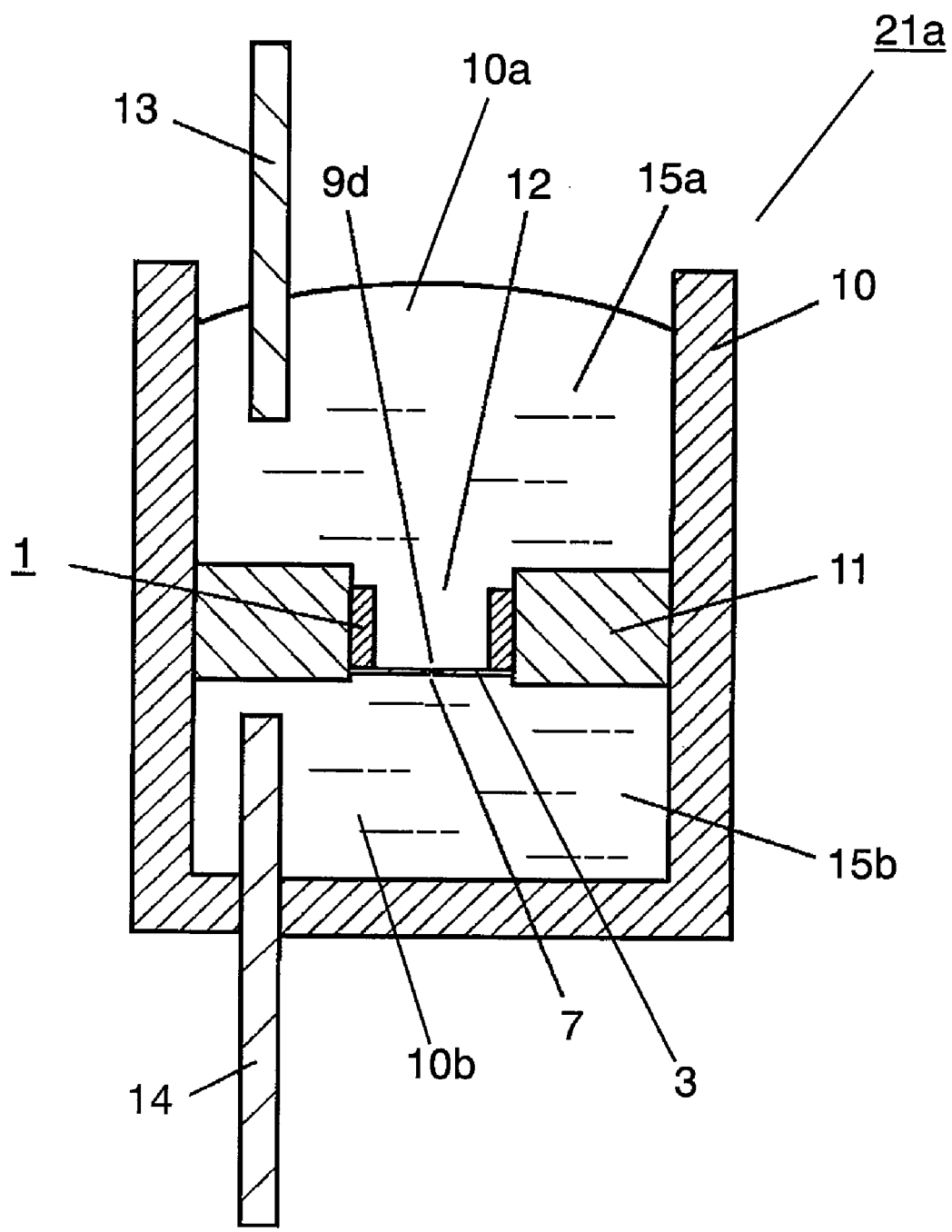
FIG. 6 is a schematic sectional view of a cellular potential measuring apparatus of another aspect in which the cellular electrophysiological measurement device shown in FIG. 1 has been placed.

In the aforementioned description of the measurement method with apparatus 21, device 1 is provided with layer 3 on its upper side. The measurement, however, can also be performed with device 1 provided with layer 3 on its lower side as shown in FIG. 6. In the case where layer 3 is provided on the lower side of device 1, cell 16 adheres to opening 9d. This design can be used when the measurement is made easier with cell 16 adhering to opening 9d, which is a pit formed on second surface 4a. It is preferable to select between these designs depending on the characteristics of cell 16.

It is also preferable that depression 8 and through-hole 9 formed in device 1 of the first embodiment are changed in diameter and length depending on the type of cell 16. Depression 8 is preferably 10 to 50 μm and more preferably 30 to 40 μm in diameter. Through-hole 9 is preferably 1 to 5 μm and more preferably 1 to 3 μm in diameter, and preferably 1 to 10 μm and more preferably 1 to 5 μm in length. Layer 3 and layer 4 should be changed in thickness depending on the shapes of depression 8 and through-hole 9; however, layer 3 is preferably thicker than layer 4 in terms of the mechanical strength of device 1. Layer 3 is preferably 5 to 30 μm thick, and layer 4 is preferably 0.5 to 3 μm thick.

In the case where a through-hole and a depression are formed in a substrate made exclusively of silicon, the cellular electrophysiological measurement device is susceptible to breakage due to its low mechanical strength. The device is also susceptible to breakage during its manufacture and during the application of suction pressure to a cell from the suction pump.

However, in the case of device 1, thin plate 7 has a laminated structure of at least two layers including layer 3 made, for example, of silicon and layer 4 made, for example, of silicon dioxide. The laminated structure allows device 1 to be a cellular electrophysiological measurement device with high mechanical strength. The structure also allows device 1 to have higher production yield without deterioration in workability. Thus, device 1 can have both a mechanical strength and high production yield.

The structure with layer 3 thicker than layer 4 allows depression 8 to be any arbitrary shape. As a result, depression 8 can be designed to make cell 16 held easily by a suction means or the like.

The formation of through-hole 9 extending between layer 3 and layer 4 can maintain the laminated structure even at the thinnest portion of thin plate 7 that is formed at bottom 8b of depression 8 around through-hole 9. As a result, device 1 can be strong against breakage.

As shown in FIGS. 1 and 2, outer periphery 4b of thin plate 7 is designed smaller than outer periphery 6a of frame (hereinafter, outer periphery 6a), which is the outer periphery of frame 6. This structure prevents thin plate 7, which is mechanically weaker than frame 6, from partly protruding beyond frame 6 so as to reduce chipping at outer periphery 4b.

The formation of rounded part 3c at edge 3b of thin plate 7 can prevent edge 3b from having chipping or other damage. This structure can minimize the generation of dust or foreign matter from the chipping of device 1 during its manufacture. Thus, this structure is effective to prevent the generation of the foreign matter.

Making layer 3 from silicon and layer 4 from silicon dioxide allows thin plate 7 and frame 6 to be processed with high precision. This structure also provides a method for manufacturing device 1 with high production yield.

The method for manufacturing device 1 will be described as follows with reference to drawings.

FIGS. 7A to 7K are sectional views showing a method for manufacturing the cellular electrophysiological measurement device of the first embodiment.

Figure 7A:
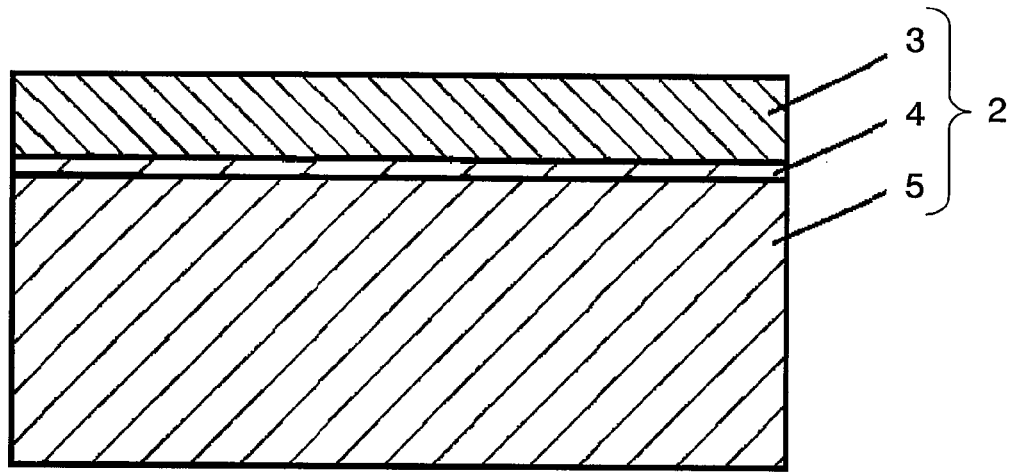
FIG. 7A is a sectional view showing a method for manufacturing the cellular electrophysiological measurement device shown in FIG. 1.

First of all, as shown in FIG. 7A, in a substrate preparation step, substrate 2 is prepared by forming a laminated structure constructing of first material layer 3 made of silicon, second material layer 4 made of silicon dioxide, and third material layer 5 made of silicon. Substrate 2 is generally called an SOI (silicon on insulator) substrate which is easily available. The SOI substrate is produced by thermally oxidizing the surface of a single-crystal silicon substrate, combining it with another single-crystal silicon substrate, and grinding the combined substrates to a predetermined thickness. Alternatively, the SOI substrate can be produced by depositing polycrystalline or amorphous silicon to a predetermined thickness by CVD or the like after thermal oxidation. In the substrate preparation step, the SOI substrate can be prepared by either of these methods.

Figure 7B:
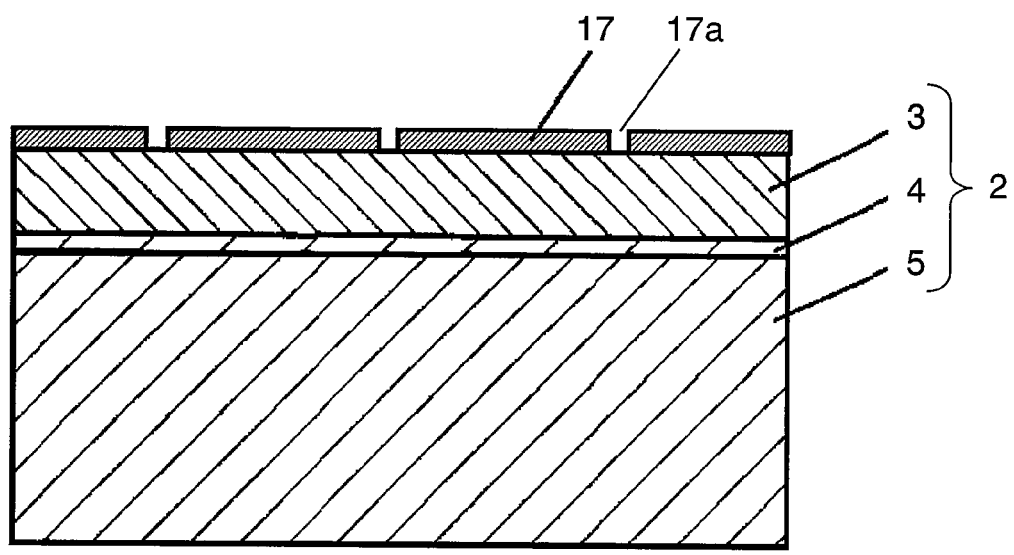
FIG. 7B is another sectional view showing the method for manufacturing the cellular electrophysiological measurement device shown in FIG. 1.

As shown in FIG. 7B, in a first-resist-film forming step, first etching resist film 17 (hereinafter, film 17) is formed on the side of first surface 3a of layer 3. Film 17 has a predetermined pattern including first resist opening 17a (hereinafter, opening 17a) or the like.

Figure 7C:
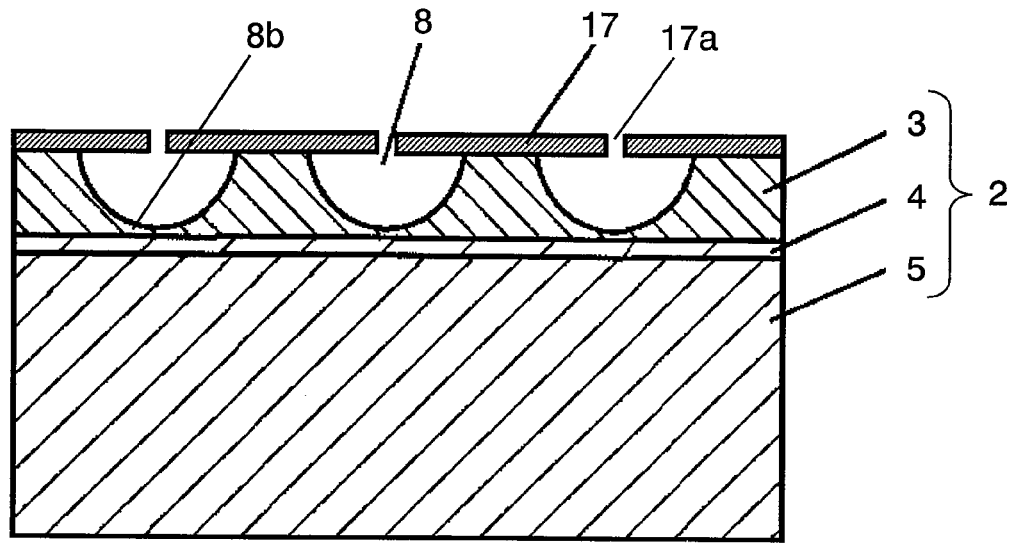
FIG. 7C is another sectional view showing the method for manufacturing the cellular electrophysiological measurement device shown in FIG. 1.

As shown in FIG. 7C, in a depression forming step, depression 8 is formed in layer 3 by etching using a first etching gas introduced from opening 17a. In the case of dry etching using plasma, $SF_6$, $CF_4$ or the like can be effectively used as the first etching gas. It is more preferable to use $XeF_2$ as the first etching gas to perform etching without the need of degrading the gas by plasma. Film 17 is hardly ever etched by $XeF_2$. As a result, the silicon forming layer 3 can be etched without causing film 17 to be etched together, thereby effectively forming depression 8.

Figure 7D:
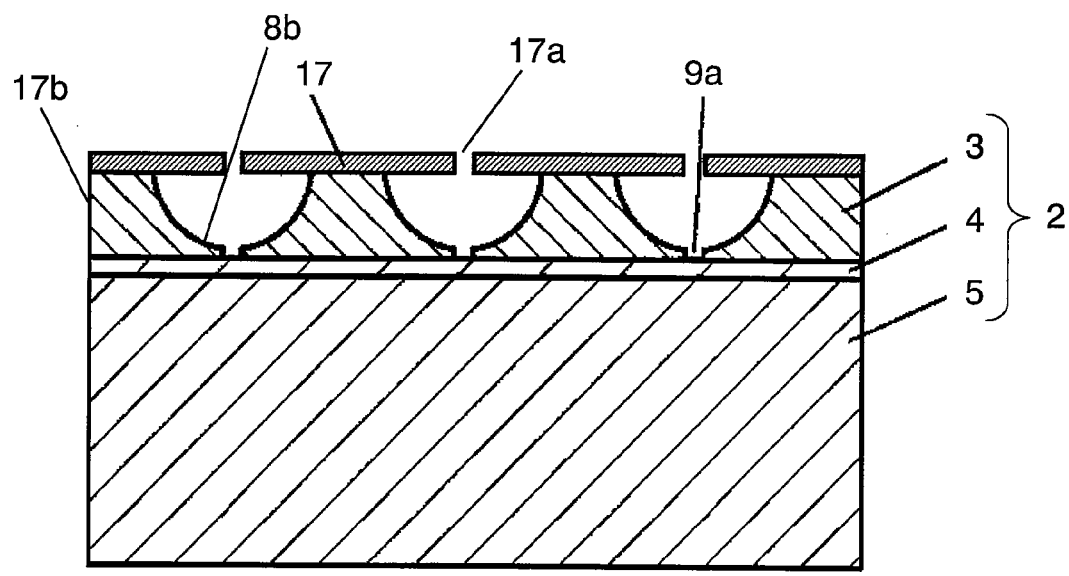
FIG. 7D is another sectional view showing the method for manufacturing the cellular electrophysiological measurement device shown in FIG. 1.
Figure 7E:
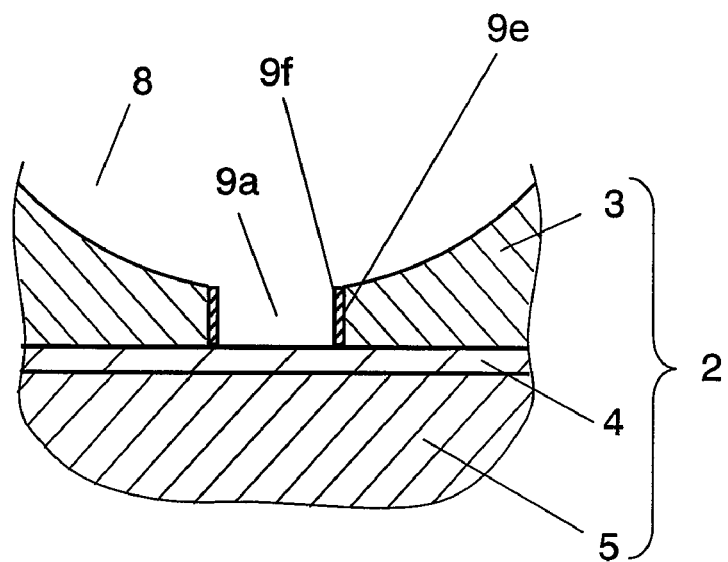
FIG. 7E is another sectional view showing the method for manufacturing the cellular electrophysiological measurement device shown in FIG. 1.

As shown in FIG. 7D, in a first-through-hole forming step, a second etching gas and a third etching gas are introduced from opening 17a. As a result, first hole 9a (hereinafter, hole 9a) is etched to reach layer 4 from bottom 8b of depression 8. In the case of dry etching using ICP plasma, it is preferable to use, for example, $SF_6$ or $CF_4$ as the second etching gas, and to use, for example, $C_4F_8$ or $CHF_3$ as the third etching gas. The second etching gas is introduced to etch silicon and the third etching gas is introduced to form protective film 9f on inner wall 9e of hole 9a thus etched as shown in FIG. 7E. The optimum combination of the second and third etching gases enables the processing phenomenon of etching to be generated exclusively beneath opening 17a. Thus, hole 9a is etched nearly perpendicular to layer 3.

Figure 7F:
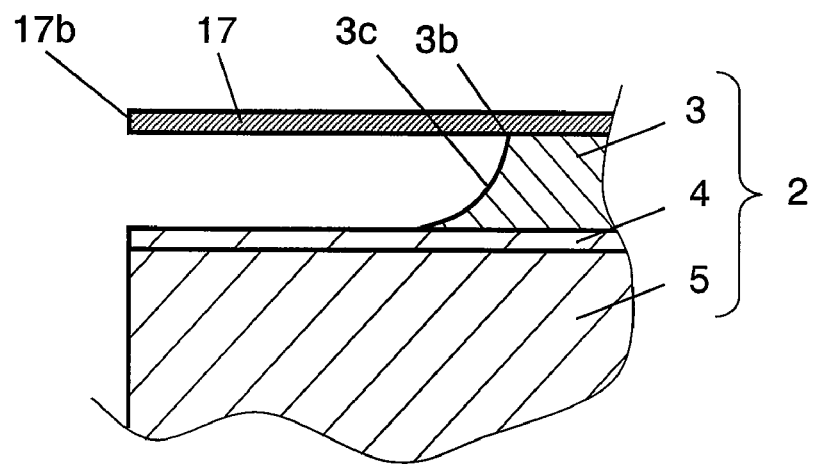
FIG. 7F is another sectional view showing the method for manufacturing the cellular electrophysiological measurement device shown in FIG. 1.

As shown in FIG. 7F, in the first-through-hole forming step, edge 3b of thin plate 7 is formed inner than edge 17b of film 17. This structure easily prevents outer periphery 4b of thin plate 7 from protruding beyond outer periphery 6a of frame 6 when frame 6 is formed in layer 5 in a later step.

Figure 7G:
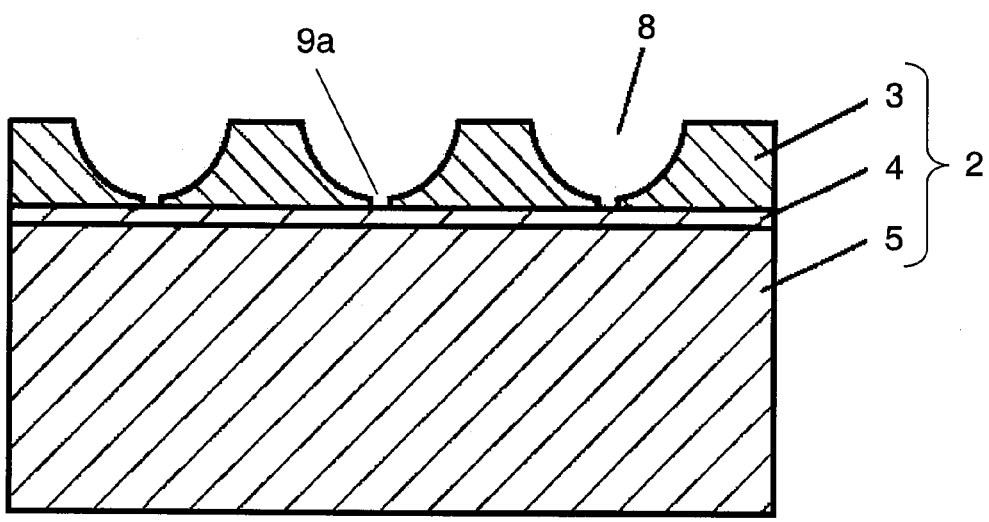
FIG. 7G is another sectional view showing the method for manufacturing the cellular electrophysiological measurement device shown in FIG. 1.

As shown in FIG. 7G, in a first-resist-film removing step, film 17 is removed.

Figure 7H:
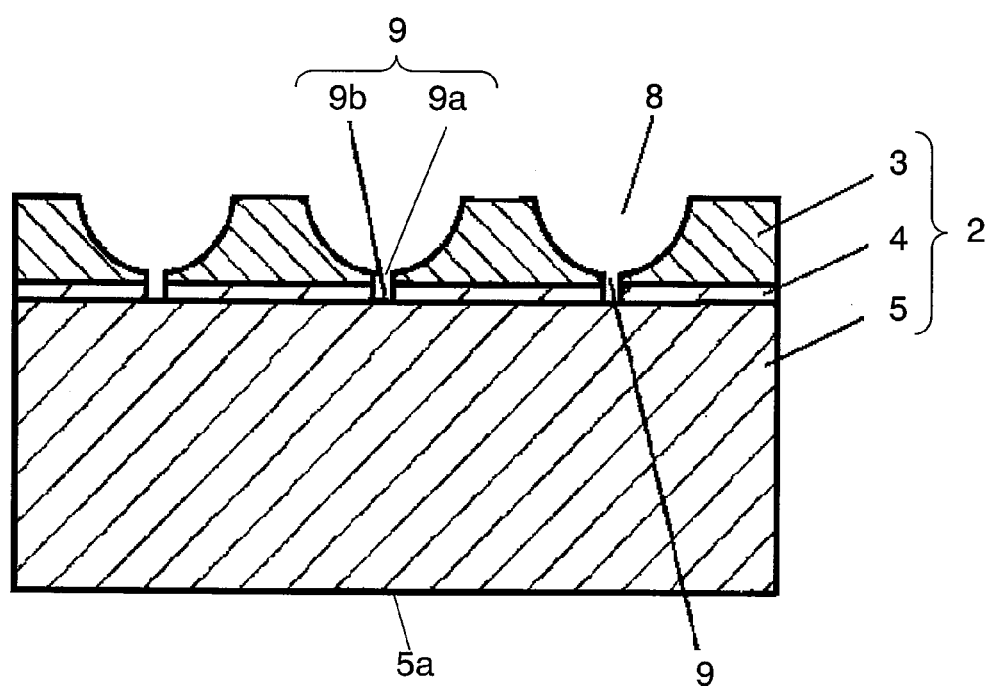
FIG. 7H is another sectional view showing the method for manufacturing the cellular electrophysiological measurement device shown in FIG. 1.

Later, as shown in FIG. 7H, in a second-through-hole forming step, etching is performed by introducing a fourth etching gas from the side of layer 3. As a result, second hole 9b (hereinafter, hole 9b) is formed in layer 4 in such a manner as to be contiguous with hole 9a formed in layer 3. The etching is preferably plasma etching using, for example, $CF_4$ or Ar as the fourth etching gas because the fourth etching gas can exclusively etch the silicon dioxide forming layer 4 without much etching the silicon forming layer 3. The etching allows hole 9b to be formed in layer 4 in almost the same shape as hole 9a formed in layer 3. Thus, hole 9a and hole 9b contiguous with hole 9a form through-hole 9. In processing hole 9b, hole 9a functions as a mask.

Figure 7I:
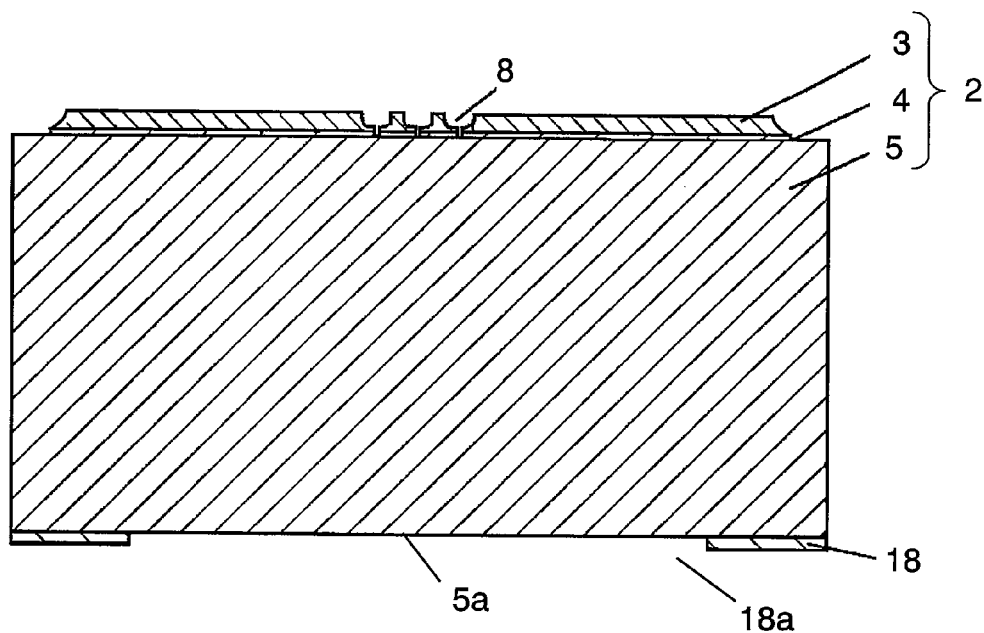
FIG. 7I is another sectional view showing the method for manufacturing the cellular electrophysiological measurement device shown in FIG. 1.

As shown in FIG. 7I, in a second-resist-film forming step, second etching resist film 18 (hereinafter, film 18) is formed on a side of third surface 5a of layer 5. Film 18 has a predetermined pattern including second resist opening 18a (hereinafter, opening 18a).

Figure 7J:
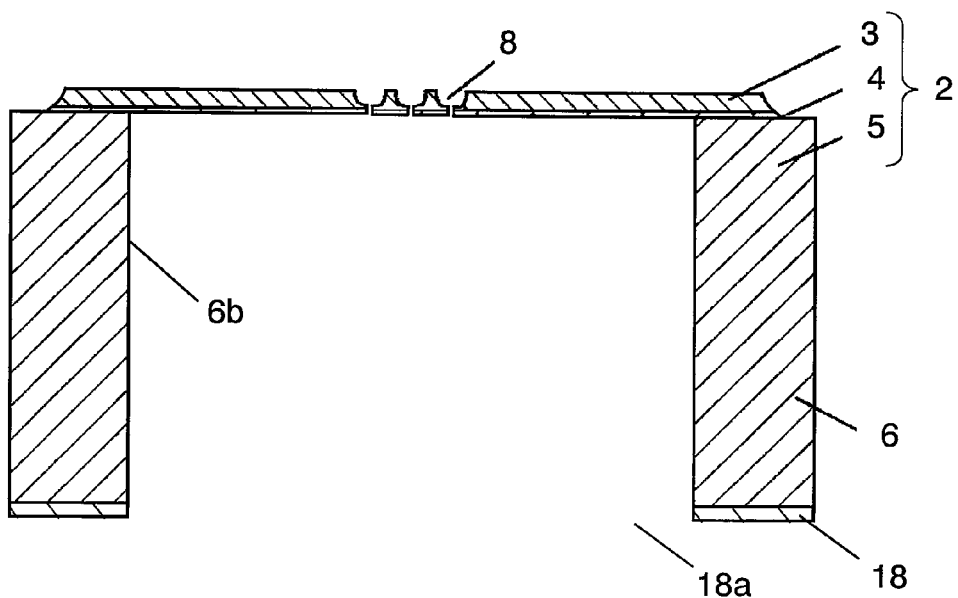
FIG. 7J is another sectional view showing the method for manufacturing the cellular electrophysiological measurement device shown in FIG. 1.

As shown in FIG. 7J, in a frame forming step, the second and third etching gases are introduced from opening 18a. As a result, the silicon forming layer 5 is etched to reach layer 4, thereby forming frame 6. This etching can be performed almost in the same manner as for forming hole 9a in the aforementioned first-through-hole forming step. As a result, the etching process of layer 5 is performed exclusively beneath opening 18a so that frame 6 can have nearly vertical inner wall 6b.

Figure 7K:
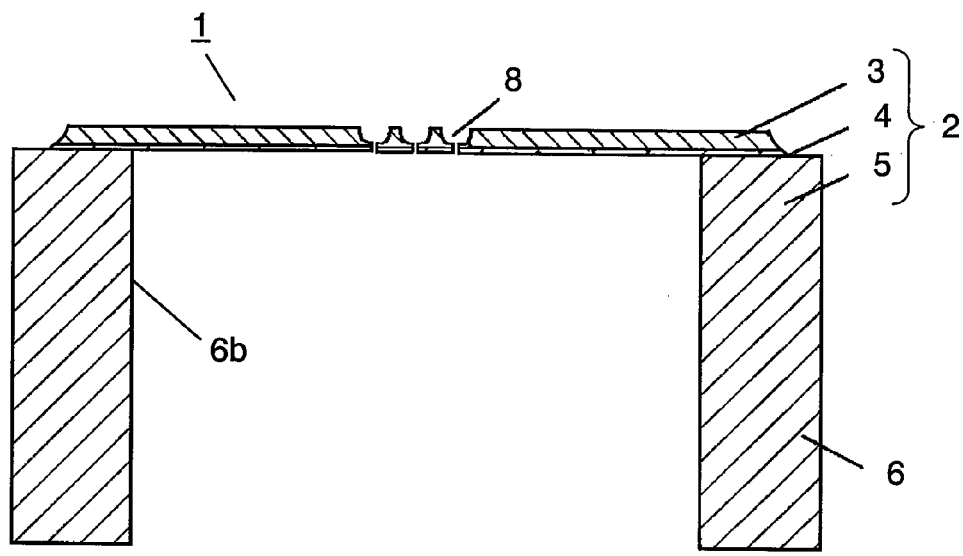
FIG. 7K is another sectional view showing the method for manufacturing the cellular electrophysiological measurement device shown in FIG. 1.

As shown in FIG. 7K, in a second-resist-film removing step, film 18 is removed.

The manufacturing method described hereinbefore is an extremely effective method because it allows the mass production of cellular electrophysiological measurement device 1 from single wafer substrate 2. In addition, the manufacturing method can greatly reduce the size of each device 1 so as to further increase the number of devices 1 manufactured from single substrate 2.

Figure 8A:
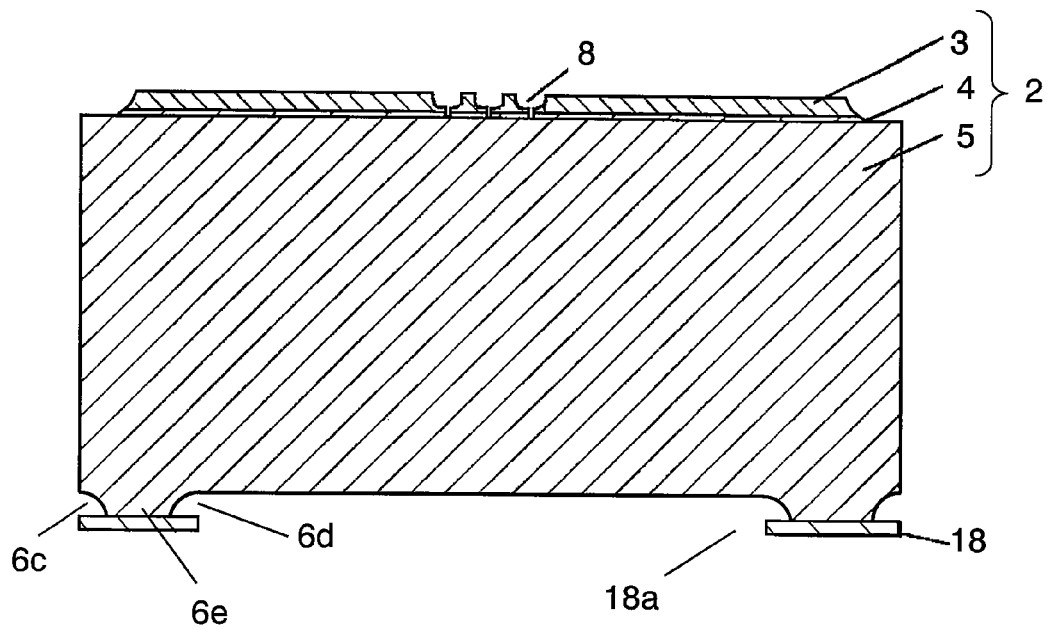
FIG. 8A is a sectional view showing a method for manufacturing a cellular electrophysiological measurement device of another aspect of the first embodiment of the present invention.

It is possible to add a first rounding-off step before the frame forming step shown in FIG. 7J. The first rounding-off step is a step for etching the surface of layer 5 to some extent by introducing the first etching gas from opening 18a as shown in FIG. 8A. The first etching gas can be, for example, XeF$_2$.

Figure 8B:
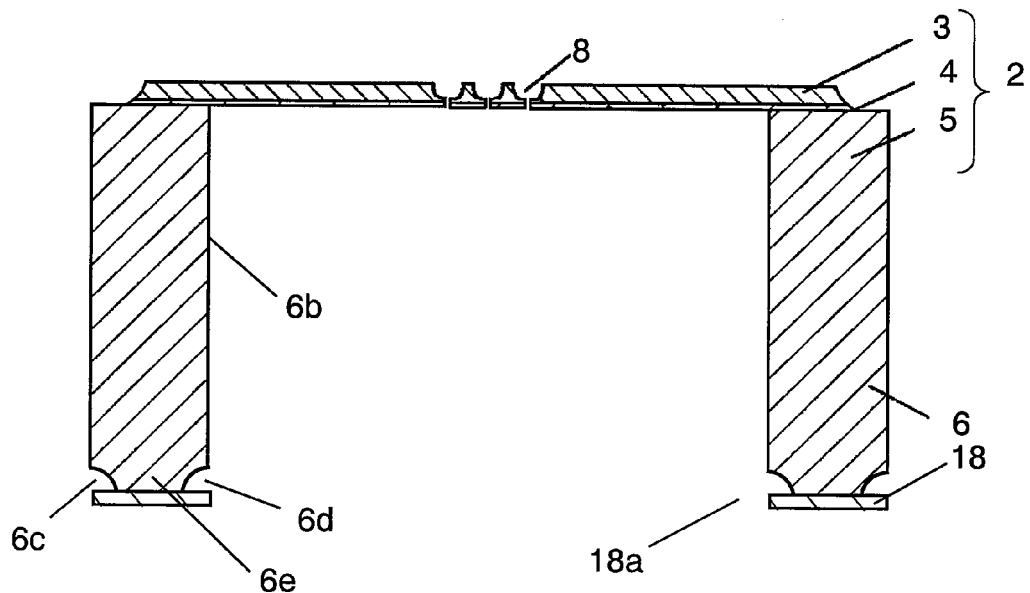
FIG. 8B is another sectional view showing the method for manufacturing the cellular electrophysiological measurement device of the aspect of the first embodiment of the present invention.

Then, as shown in FIG. 8B, in the frame forming step, etching is performed by introducing the second and third etching gases from opening 18a.

Figure 8C:
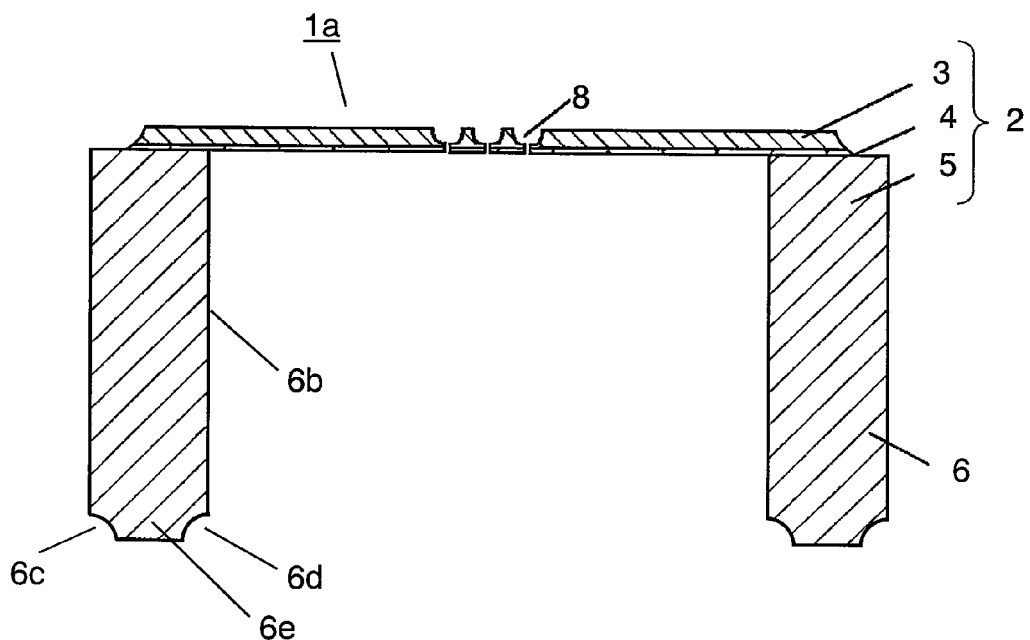
FIG. 8C is another sectional view showing the method for manufacturing the cellular electrophysiological measurement device of the aspect of the first embodiment of the present invention.

In the second-resist-film removing step, film 18 is removed. As shown in FIG. 8C, outer peripheral edge 6c and inner wall edge 6d of frame 6 are rounded off to some extent. Rounding off outer peripheral edge 6c and inner wall edge 6d in this manner results in rounding off lower edge 6e to some extent. This structure prevents lower edge 6e of frame 6 from having chipping or other damage, thereby providing cellular electrophysiological measurement device 1a which has less chipping and hence less dust or foreign matter than device 1.

Figure 9A:
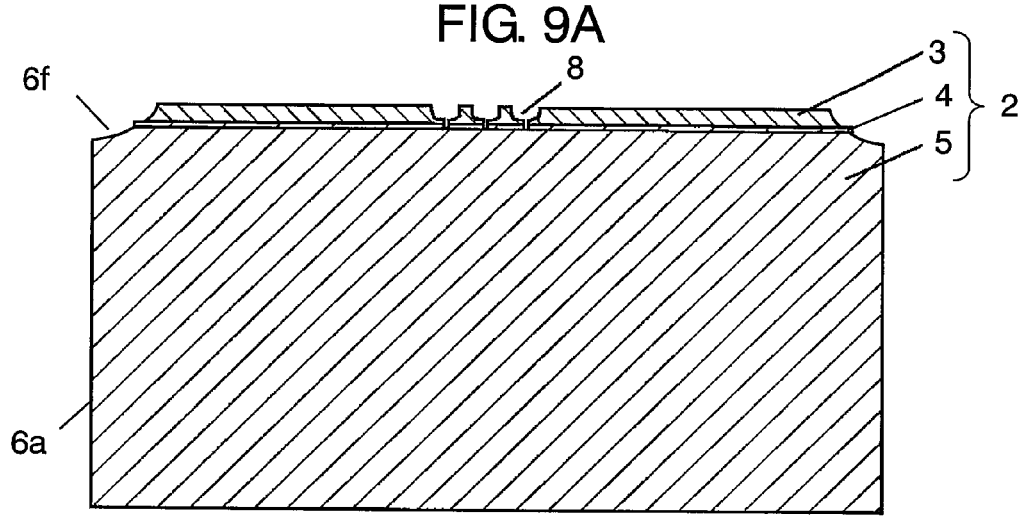
FIG. 9A is a sectional view showing a method for manufacturing a cellular electrophysiological measurement device of another aspect of the first embodiment of the present invention.
Figure 9B:
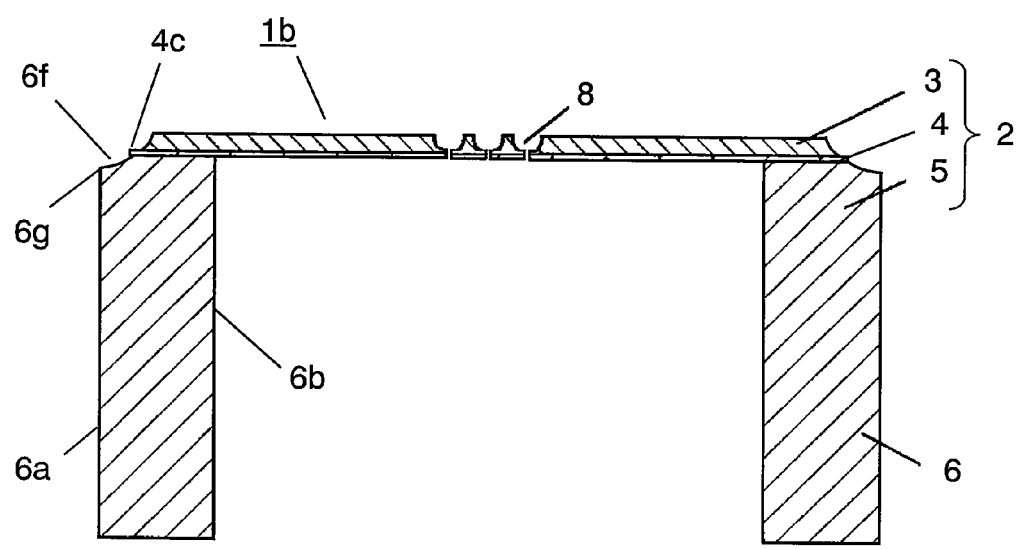
FIG. 9B is another sectional view showing the method for manufacturing the cellular electrophysiological measurement device of the aspect of the first embodiment of the present invention.

It is also possible to add a second rounding-off step after the second-through-hole forming step shown in FIG. 7H. In the second rounding-off step, the first etching gas is introduced for moderately rounding off top edge 6f of outer periphery 6a of layer 5, as shown in FIG. 9A. The first etching gas can be, for example, XeF$_2$. After this, the second-resist-film forming step, the frame forming step, and the second-resist-film removing step are performed as described above. As a result, as shown in FIG. 9B, top edge 6f of frame 6 is rounded off, thereby providing cellular electrophysiological measurement device 1b not so vulnerable to chipping or other damage. In the second rounding-off step, edge 4c of layer 4 may be slightly protruded due to the etching of top edge 6f, but edge 4c is located too far from corner 6g of frame 6 to be damaged.

Figure 9C:
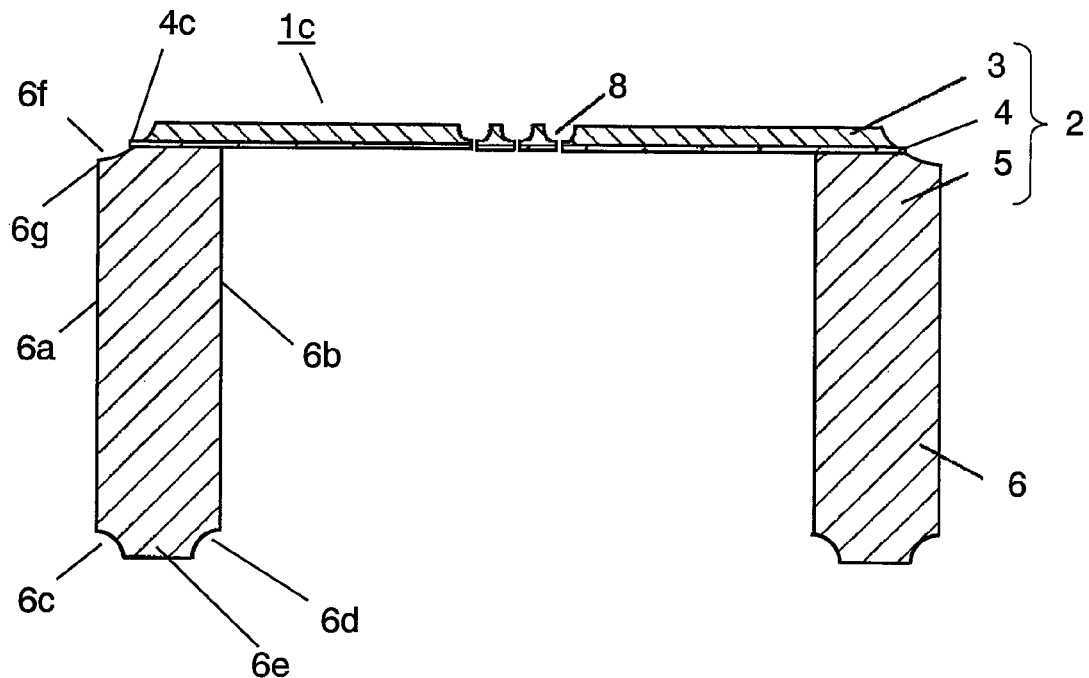
FIG. 9C is another sectional view showing the method for manufacturing the cellular electrophysiological measurement device of the aspect of the first embodiment of the present invention.

It is also possible to add both the first rounding-off step and the second rounding-off step. The addition of these steps provides cellular electrophysiological measurement device 1c not so vulnerable to chipping or other damage at top edge 6f and lower edge 6e as shown in FIG. 9C. Thus, cellular electrophysiological measurement device 1c can have less chipping and hence less dust or foreign matter than devices 1, 1a, and 1b.

Second Exemplary Embodiment

A cellular electrophysiological measurement device of a second embodiment and a method for manufacturing the device will be described as follows with reference to drawings.

Figure 10:
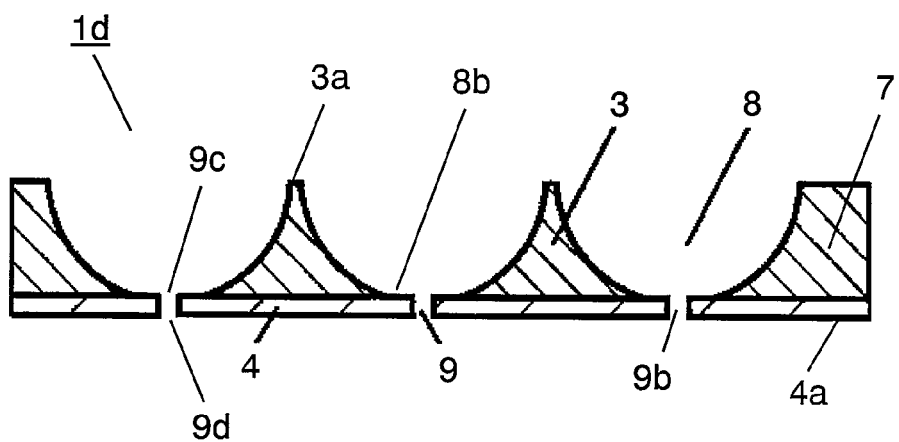
FIG. 10 is an enlarged sectional view of an essential part of a cellular electrophysiological measurement device of a second embodiment of the present invention.

FIG. 10 is a sectional view of the cellular electrophysiological measurement device of the second embodiment. FIGS. 11A to 11H are sectional views showing a method for manufacturing the device shown in FIG. 10. Cellular electrophysiological measurement device 1d (hereinafter, device 1d) of the second embodiment differs from device 1 of the first embodiment in that as shown in FIG. 10, depression 8 is formed in first material layer 3, and through-hole 9 is formed in second material layer 4. In other words, through-hole 9 consists exclusively of second hole 9b formed in layer 4. This structure can reduce the length of through-hole 9 and the thickness of thin plate 7, so that in the case where cell 16 is large or flat in shape, the adhesion between cell 16 and thin plate 7 can be further improved.

Device 1d can be used in the same manner as in the first embodiment, and therefore, the description of its use will be omitted.

The method for manufacturing cellular electrophysiological measurement device 1d of the second embodiment will be described with reference to FIGS. 11A to 11H.

Figure 11A:
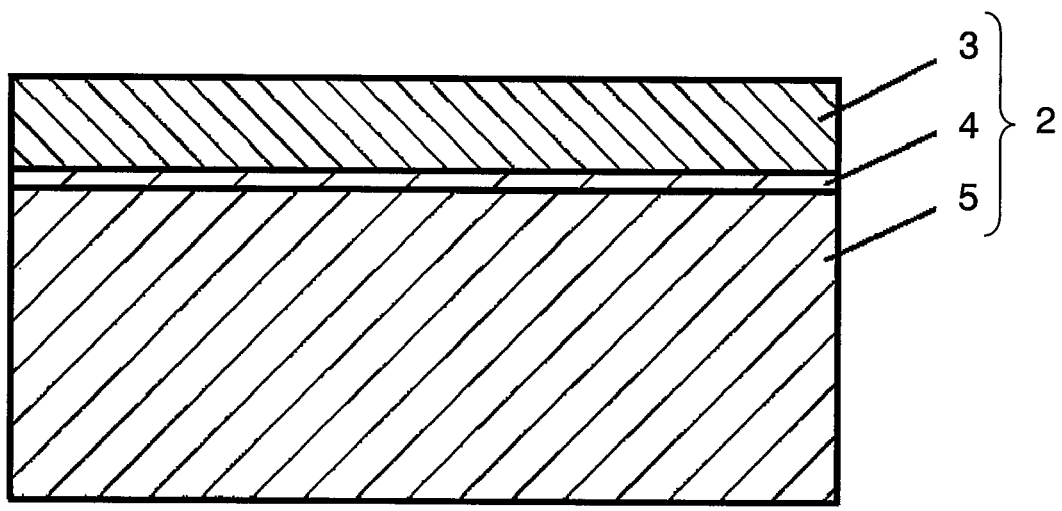
FIG. 11A is a sectional view showing a method for manufacturing the cellular electrophysiological measurement device shown in FIG. 10.

First of all, as shown in FIG. 11A, in a substrate preparation step, substrate 2 is prepared by forming a laminated structure constructing of first material layer 3 made of silicon, second material layer 4 made of silicon dioxide, and third material layer 5 made of silicon. Substrate 2 is generally called an SOI (silicon on insulator) substrate which is easily available.

Figure 11B:
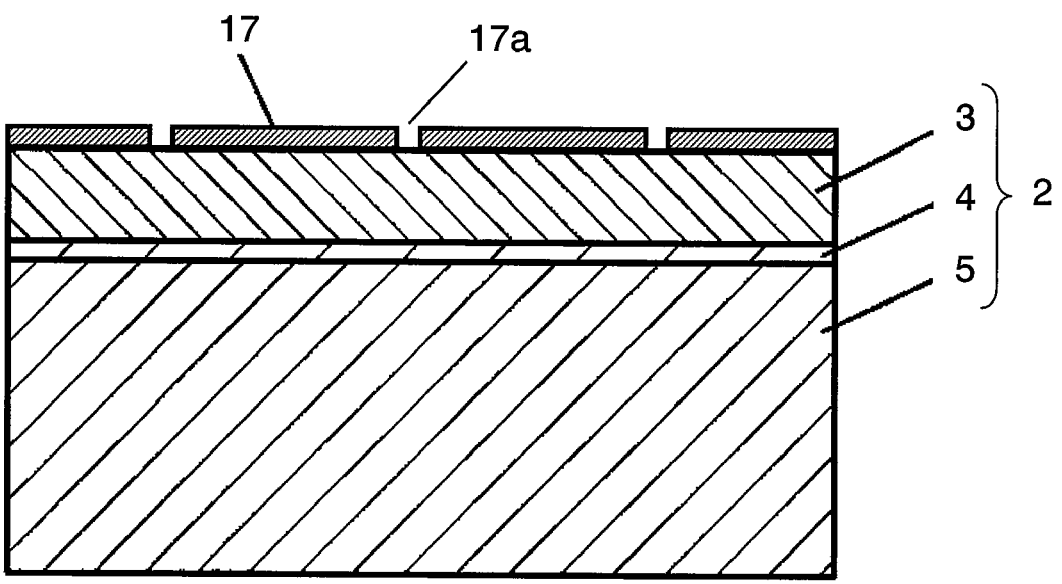
FIG. 11B is another sectional view showing the method for manufacturing the cellular electrophysiological measurement device shown in FIG. 10.

As shown in FIG. 11B, in a first-resist-film forming step, first etching resist film 17 is formed on the first surface 3a side of layer 3. Film 17 has a predetermined pattern including first resist opening 17a.

Figure 11C:
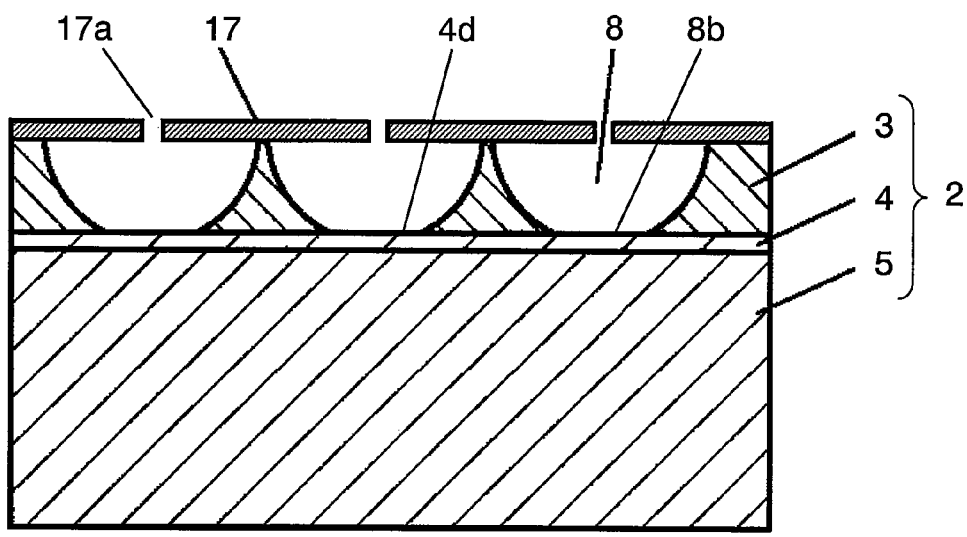
FIG. 11C is another sectional view showing the method for manufacturing the cellular electrophysiological measurement device shown in FIG. 10.

As shown in FIG. 11C, in a depression forming step, depression 8 is formed in layer 3 by etching using a first etching gas introduced from opening 17a. In the case of dry etching using plasma, as in the first embodiment, XeF$_2$ gas can be effectively used as the first etching gas to form depression 8.

The method for manufacturing device 1d of the second embodiment differs from the method of the first embodiment as follows. In the depression forming step, the etching of depression 8 by the first etching gas is performed to reach as far as the surface of layer 4 so as to make depression 8 sufficiently large. Furthermore, bottom 8b of depression 8 is made flat, or in other words, top surface 4d of layer 4 is exposed to become bottom 8b. In the case where cell 16 has a flat shape, cell 16 is tightly adhered to flat bottom 8b so as to improve the adhesion between cell 16 and thin plate 7. As a result, cell 16 having a large size can be measured with improved precision.

Figure 11D:
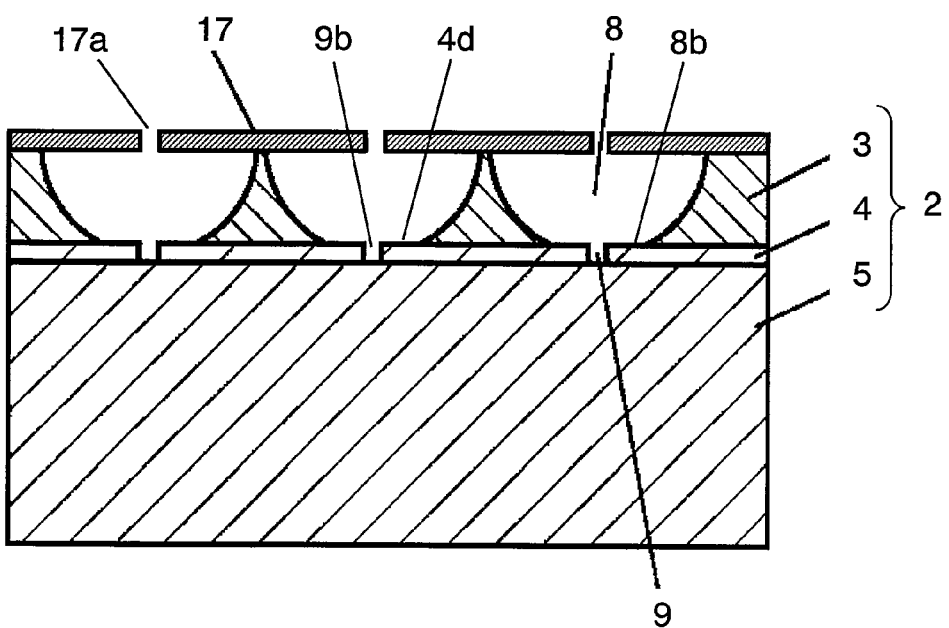
FIG. 11D is another sectional view showing the method for manufacturing the cellular electrophysiological measurement device shown in FIG. 10.

As shown in FIG. 11D, in a second-through-hole forming step, etching is performed by introducing a fourth etching gas from opening 17a so as to form hole 9b in layer 4. The etching is preferably plasma etching using, for example, CF$_4$ or Ar as the fourth etching gas, because the fourth etching gas can exclusively etch the silicon dioxide forming layer 4 without much etching the silicon forming layer 3. Thus, hole 9b is formed right beneath opening 17a using opening 17a as a mask. In device 1d, hole 9b forms through-hole 9.

Film 17 is required to be resistant to the plasma etching performed using the fourth etching gas, and therefore, is preferably made of aluminum, silicon nitride, or the like.

Figure 11E:
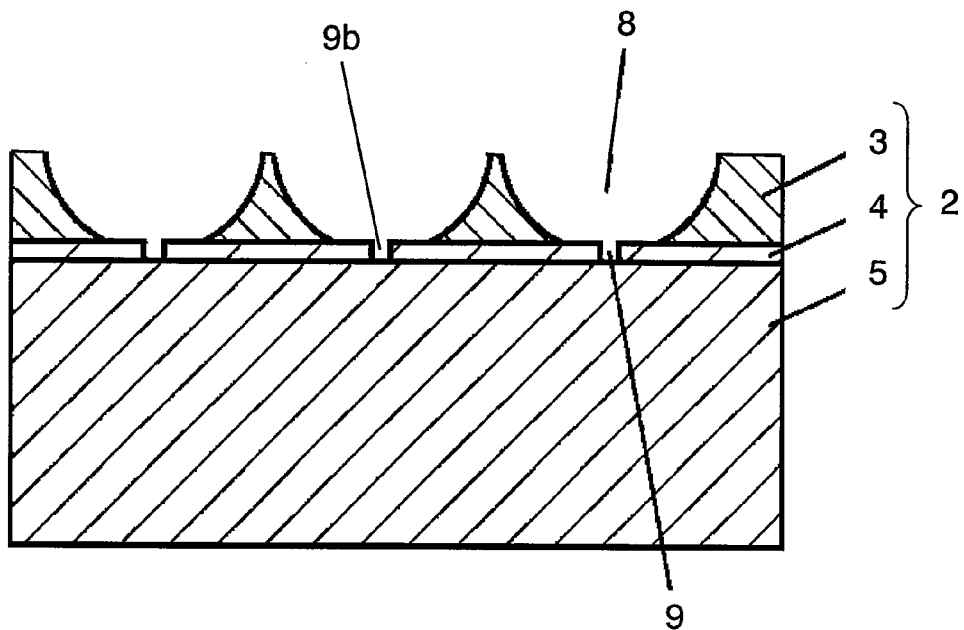
FIG. 11E is another sectional view showing the method for manufacturing the cellular electrophysiological measurement device shown in FIG. 10.

As shown in FIG. 11E, in a first-resist-film removing step, film 17 is removed.

Figure 11F:
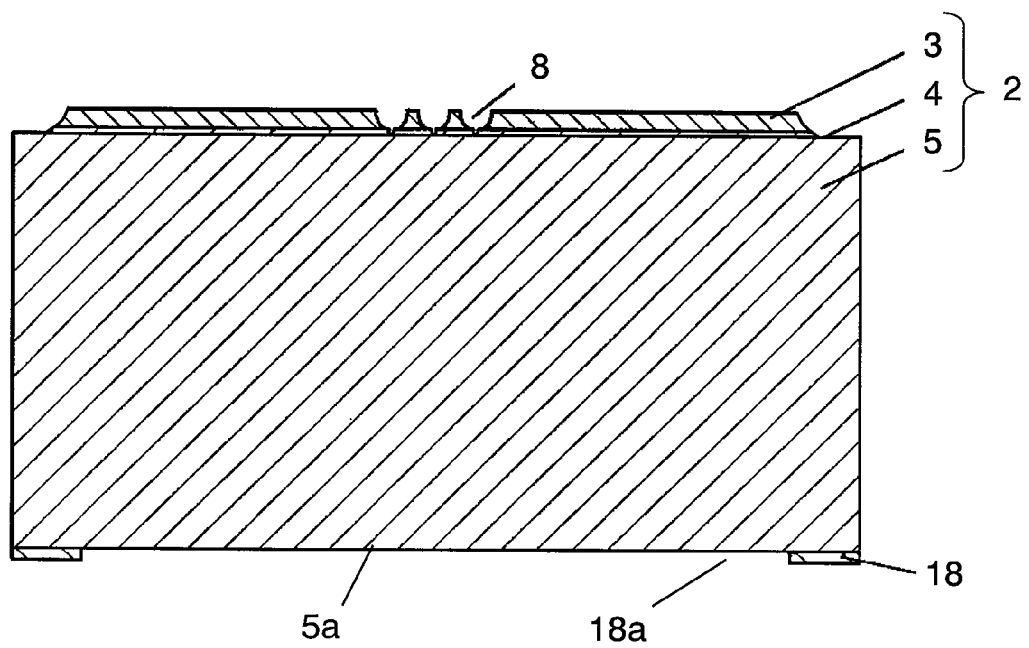
FIG. 11F is another sectional view showing the method for manufacturing the cellular electrophysiological measurement device shown in FIG. 10.

As shown in FIG. 11F, in a second-resist-film forming step, second etching resist film 18 is formed on the side of third surface 5a of layer 5 as in the first embodiment. Film 18 has a predetermined pattern including second resist opening 18a.

Figure 11G:
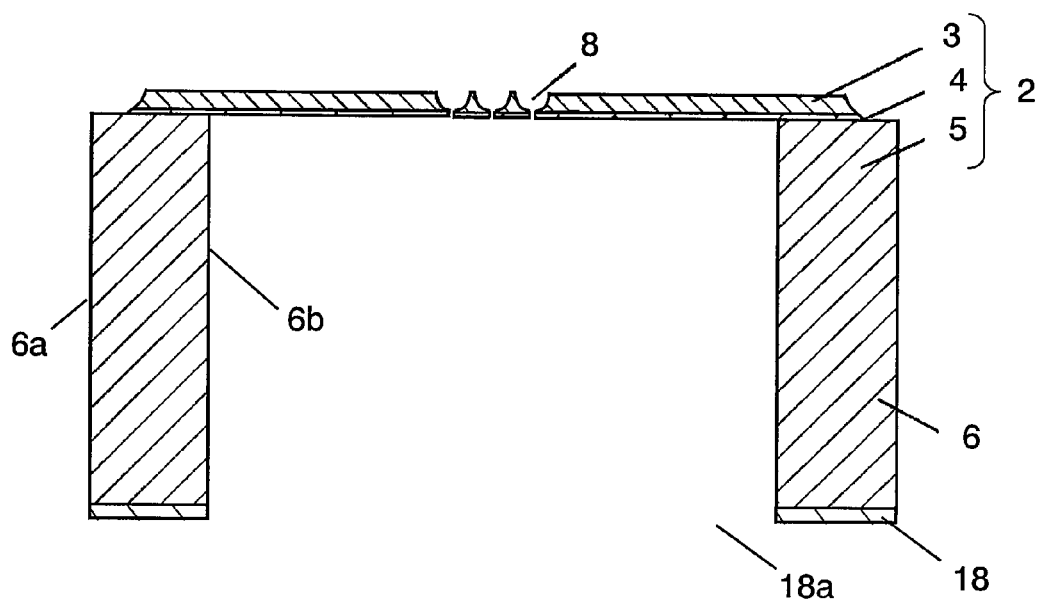
FIG. 11G is another sectional view showing the method for manufacturing the cellular electrophysiological measurement device shown in FIG. 10.

As shown in FIG. 11G, in a frame forming step, a second etching gas and a third etching gas are introduced from opening 18a. As a result, layer 5 is etched to reach layer 4 so as to form frame 6 as in the first embodiment.

Figure 11H:
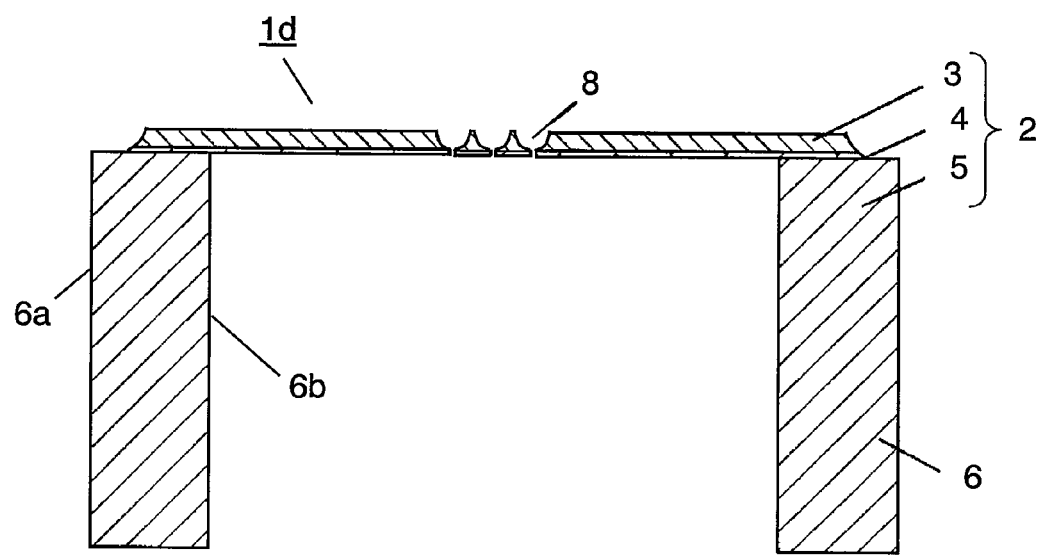
FIG. 11H is another sectional view showing the method for manufacturing the cellular electrophysiological measurement device shown in FIG. 10.

As shown in FIG. 11H, in a second-resist-film removing step, film 18 is removed. This results in cellular electrophysiological measurement device 1d of the second embodiment.

Figure 12A:
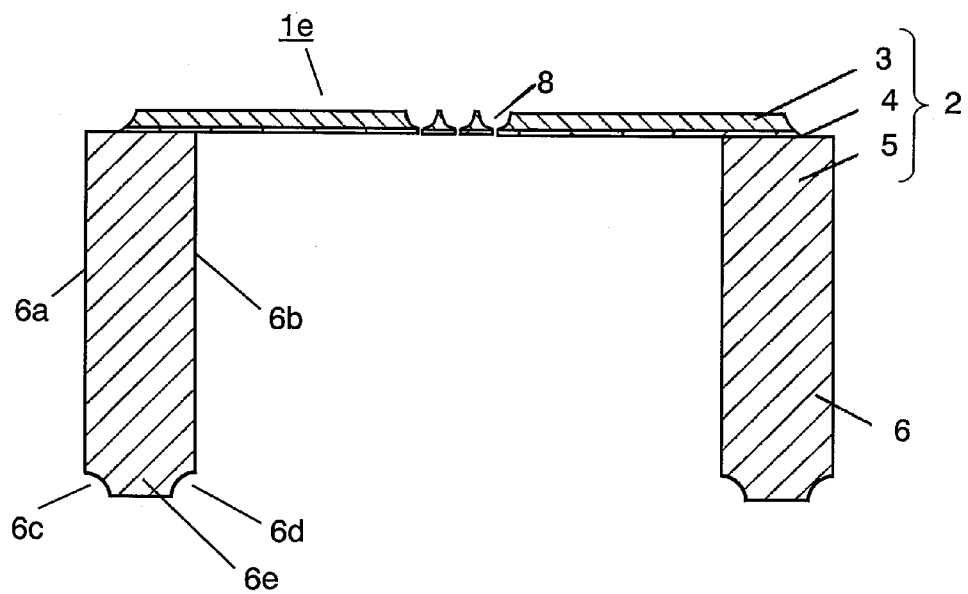
FIG. 12A is a sectional view showing a method for manufacturing a cellular electrophysiological measurement device of another aspect of the second embodiment of the present invention.

It is possible to add a first rounding-off step before the frame forming step shown in FIG. 11G in the same manner as in the first embodiment. The first rounding-off step is a step for etching the surface of layer 5 to some extent by introducing the first etching gas from opening 18a. The first etching gas can be, for example, XeF$_2$. This results in cellular electrophysiological measurement device 1e in which outer peripheral edge 6c and inner wall edge 6d of frame 6 are rounded off to some extend as shown in FIG. 12A.

Figure 12B:
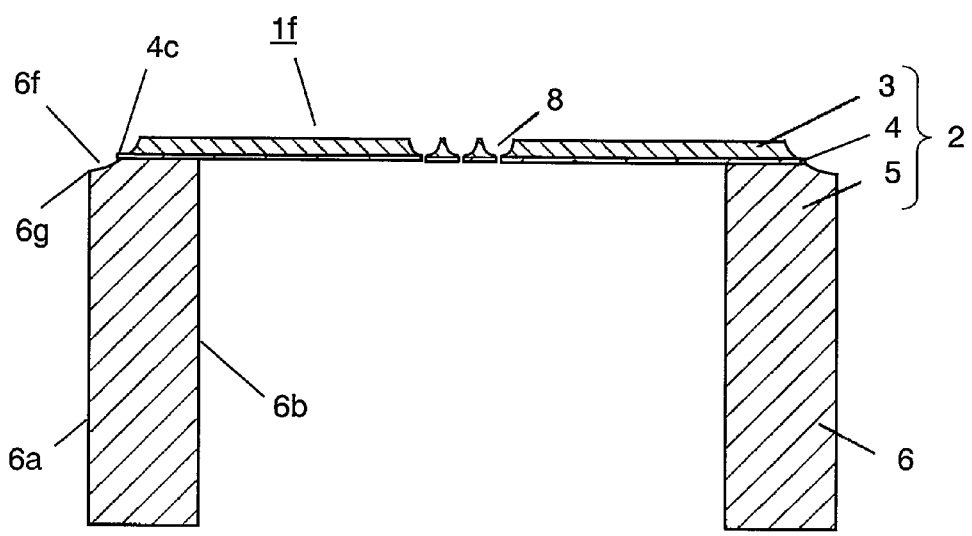
FIG. 12B is another sectional view showing the method for manufacturing the cellular electrophysiological measurement device of the aspect of the second embodiment of the present invention.

It is also possible to add a second rounding-off step after the second-through-hole forming step shown in FIG. 11D. In the second rounding-off step, the first etching gas is introduced for moderately rounding off top edge 6f of outer periphery 6a of layer 5. The first etching gas can be, for example, XeF$_2$. The addition of the second rounding-off step provides cellular electrophysiological measurement device 1f in which top edge 6f of outer periphery of frame 6 is rounded off to some extent as shown in FIG. 12B. As described above, cellular electrophysiological measurement device 1f is not so vulnerable to chipping or other damage at top edge 6f of frame 6. In the second rounding-off step, edge 4c of layer 4 may be slightly protruded due to the etching of top edge 6f, but edge 4c is located too far from corner 6g of frame 6 to be damaged.

Figure 12C:
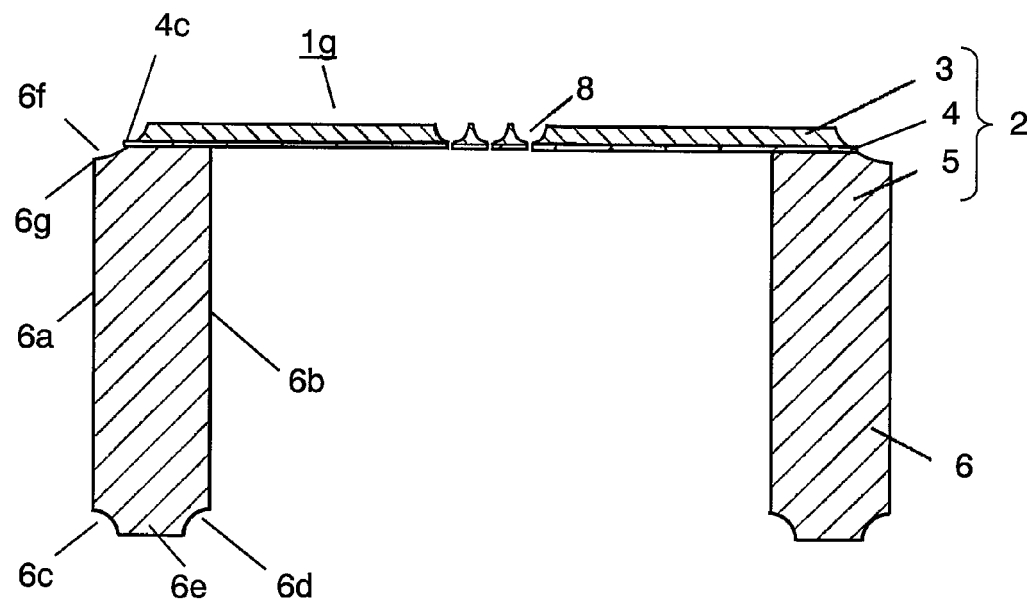
FIG. 12C is another sectional view showing the method for manufacturing the cellular electrophysiological measurement device of the aspect of the second embodiment of the present invention.

It is also possible to add both the first rounding-off step and the second rounding-off step. The addition of these steps provides cellular electrophysiological measurement device 1g not so vulnerable to chipping or other damage at top edge 6f and lower edge 6e as shown in FIG. 12C. Thus, cellular electrophysiological measurement device 1g can have less chipping and hence less dust or foreign matter than devices 1d, 1e, and 1f.

Third Exemplary Embodiment

A cellular electrophysiological measurement device of a third embodiment and a method for manufacturing the device will be described as follows with reference to drawings.

Figure 13:
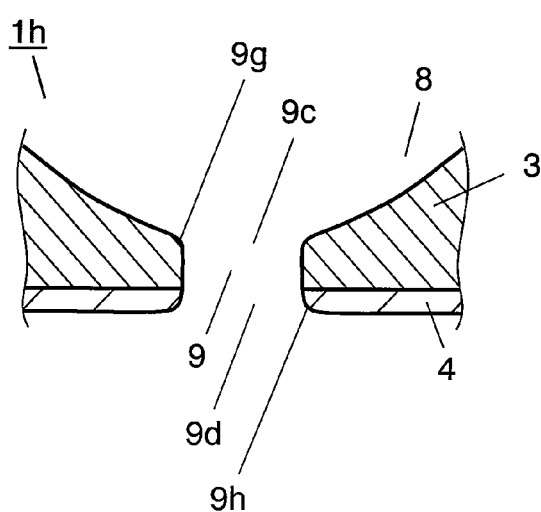
FIG. 13 is an enlarged sectional view of an essential part of a cellular electrophysiological measurement device of a third embodiment of the present invention.
Figure 14:
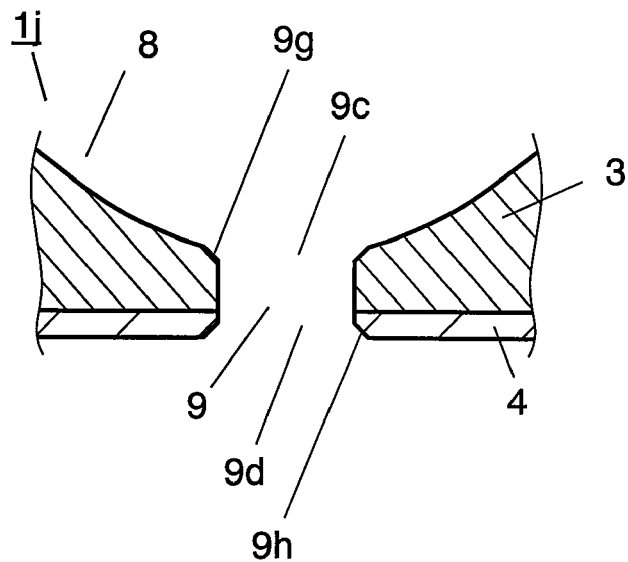
FIG. 14 is an enlarged sectional view of an essential part of a cellular electrophysiological measurement device of another aspect of the third embodiment of the present invention.

FIG. 13 is an enlarged sectional view of an essential part of the cellular electrophysiological measurement device of the third embodiment. FIG. 14 is an enlarged sectional view of an essential part of a cellular electrophysiological measurement device of another aspect of the third embodiment.

The cellular electrophysiological measurement device of the third embodiment differs from device 1 shown in the first embodiment in the shape of edge 9g of opening 9c and the shape of edge 9h of opening 9d in through-hole 9.

As shown in FIG. 13, edge 9g and edge 9h are rounded off around the entire perimeter of openings 9c and 9d. This structure of cellular electrophysiological measurement device 1h can prevent cell 16 from being damaged when it is measured with cellular potential measuring apparatus 21 or 21a described with reference to FIGS. 4 to 6. More specifically, the surface membrane of cell 16 is not inadvertently damaged when cell 16 is sucked and held from the side of lower part 10b of vessel 10 because of the round shape of edge 9g which comes into contact with cell 16. This structure enables cellular electrophysiological measurement device 1h to securely hold cell 16.

As shown in FIG. 14, edge 9g and edge 9h can be outwardly tapered by being rounded off around the entire perimeter of openings 9c and 9d. The tapering of cellular electrophysiological measurement device 1j can prevent the damage of cell 16 in the same manner as in device 1h when measured with cellular potential measuring apparatus 21 or 21a described with reference to FIGS. 4 to 6. More specifically, the surface membrane of cell 16 is not inadvertently damaged when cell 16 is sucked and held from the side of lower part 10b of vessel 10 because of the tapered shape of edge 9g which comes into contact with cell 16. This structure enables cellular electrophysiological measurement device 1j to securely hold cell 16.

Cellular electrophysiological measurement devices 1h and 1j having these structures can be easily obtained by adding a grinding step as a first smoothing step to the method for manufacturing the cellular electrophysiological measurement device described in the first or the second embodiment. In other words, substrate 2 processed by the aforementioned manufacturing method is soaked in an aqueous solution containing abrasive grains and subjected to ultrasonic vibration.

In the case where through-hole 9 has an inner diameter reduced gradually toward layer 5 so as to be pointed in shape, the edge of through-hole 9 on the side of opening 9d is acute. If cell 16 comes into contact with opening 9d with the acute edge from the side of layer 5, the membrane of cell 16 is vulnerable to the acute edge of through-hole 9.

In contrast, adding the first smoothing step to the method for manufacturing the cellular electrophysiological measurement device provides device 1h with rounded edges 9g and 9h as shown in FIG. 13. It also provides device 1j with tapered at edges 9g and 9h as shown in FIG. 14. When substrate 2 is soaked in the aqueous solution containing abrasive grains and subjected to ultrasonic vibration, the abrasive grains in the solution come into contact with the edge of through-hole 9, thereby grinding the acute portion. In the first smoothing step, not only the edge of through-hole 9, but also the other surface portion of substrate 2 is smoothed. Adding the first smoothing step to smooth the surfaces of edges 9g and 9h in this manner after the frame forming step or any other point in the process facilitates the manufacture of devices 1h and 1j used to measure cell 16 without damaging cell 16.

It is possible to provide a second smoothing step using a laser beam in manufacturing cellular electrophysiological measurement devices 1h and 1j. In the second smoothing step, a laser beam is applied to through-hole 9 from the side of either layer 3 or layer 5 so as to melt inner wall 9e and edges 9g, 9h of through-hole 9. Melting inner wall 9e and edges 9g, 9h is effective to manufacture devices 1h and 1j. In the second smoothing step, the application of the laser beam to layer 3 or layer 4 causes it to generate heat, thereby melting the material forming layer 3 or layer 4. The materials of layer 3 can be, for example, silicon and the material of layer 4 can be, for example, silicon dioxide. Thus melting layer 3 or layer 4 allows edges 9g and 9h of through-hole 9 to be changed from being acute in shape to rounded-off or tapered. Adding the second smoothing step to smooth the surfaces of edges 9g and 9h in this manner after the frame forming step or any other point in the process facilitates the manufacture of devices 1h and 1j used to measure cell 16 without damaging cell 16. When the laser beam is applied from the side of layer 3, inner wall 9e and edge 9g provided at the side of hole 9a efficiently melted. On the other hand, when the laser beam is applied from the side of layer 5, inner wall 9e and edge 9h provided at the side of hole 9b are efficiently melted.

It is also possible to provide a third smoothing step using plasma etching in manufacturing cellular electrophysiological measurement devices 1h and 1j. In the third smoothing step, plasma etching is applied to through-hole 9 from the side of either layer 3 or layer 5 so as to etch inner wall 9e and edges 9g, 9h of through-hole 9. In addition to inner wall 9e and edges 9g, 9h, the other surface of substrate 2 is smoothed. In the third smoothing step, it is preferable to use, for example, Ar gas as an etching gas. In the case of plasma etching using Ar gas, Ar plasma can be concentrated in the edges of openings 9c and 9d of through-hole 9, thereby facilitating the formation of round edges 9g and 9h. Furthermore, proper selection of the conditions of the plasma etching facilitates the formation of edges 9g and 9h tapered toward layer 5 around the entire perimeter of openings 9c and 9d. Adding the third smoothing step to smooth the surfaces of edges 9g and 9h in this manner after the frame forming step or any other point in the process facilitates the manufacture of devices 1h and 1j used to measure cell 16 without damaging cell 16.

It is also possible to provide a fourth smoothing step using chemical etching in manufacturing cellular electrophysiological measurement devices 1h and 1j. In the fourth smoothing step, the chemical etching can be effectively performed for a predetermined period with substrate 2 soaked in an etching aqueous solution. In the case where layer 4 is made of silicon dioxide, the etching aqueous solution is selected from hydrofluoric acid, ammonium bifluoride, an aqueous ammonium solution, a sodium hydroxide solution, a potassium hydroxide solution, a lithium hydroxide solution, and the like. Consequently, the acute edges of openings 9c and 9d of through-hole 9 are processed into rounded edges 9g and 9h. The fourth smoothing step further provides the effect of processing second surface 4a of layer 4 into a smooth flat shape. In addition to inner wall 9e, edges 9g, 9h, and second surface 4a, the other surface portion of substrate 2 is also smoothed. Adding the fourth smoothing step to smooth the surfaces of edges 9g and 9h in this manner after the frame forming step or any other point in the process facilitates the manufacture of devices 1h and 1j used to measure cell 16 without damaging cell 16.

Figure 15:
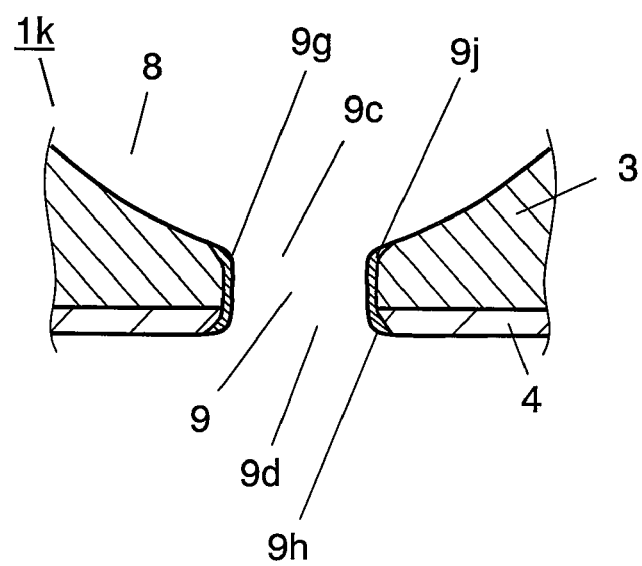
FIG. 15 is an enlarged sectional view of an essential part of a cellular electrophysiological measurement device of another aspect of the third embodiment of the present invention.

It is also possible to manufacture cellular electrophysiological measurement device 1k shown in FIG. 15 by providing a protective-layer forming step to form a protective layer on the surface of through-hole 9. In the protective-layer forming step, protective layer 9j made of an electrical insulating material is applied from the side of either layer 3 or layer 5. More specifically, protective layer 9j can be made of a metal oxide such as a silicon dioxide or a titanium dioxide by CVD, sputtering, or other method. Protective layer 9j makes the surfaces of edges 9g and 9h smooth. Adding the protective-layer forming step in this manner after the frame forming step or any other point in the process facilitates the manufacture of device 1k used to measure cell 16 without damaging cell 16.

The combination of the first, second, third, and fourth smoothing steps and the protective-layer forming step could perform more efficient surface processing. The combination of these steps facilitates the manufacture of a cellular electrophysiological measurement device used to measure cell 16 without damaging cell 16.

Fourth Exemplary Embodiment

A cellular electrophysiological measurement device of a fourth embodiment and a method for manufacturing the device will be described as follows with reference to drawings.

Figure 16:
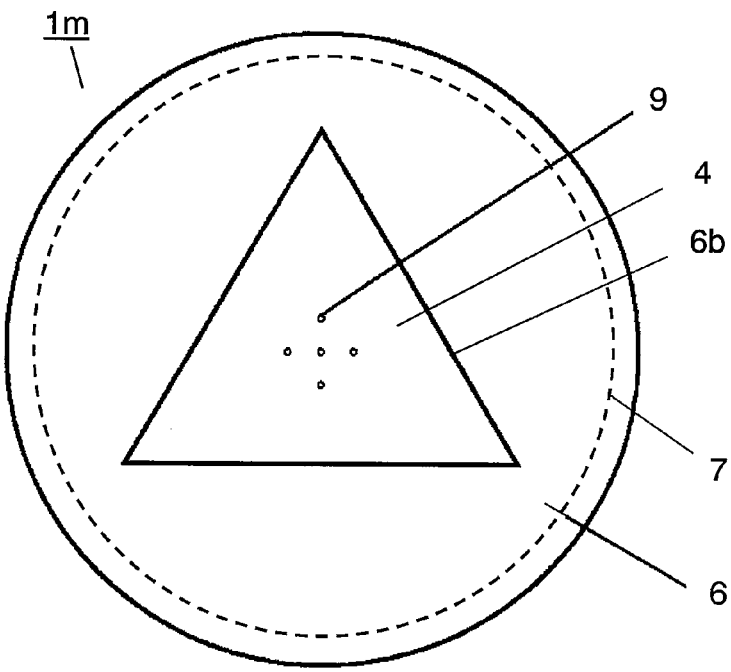
FIG. 16 is an enlarged plan view of an essential part of a cellular electrophysiological measurement device of a fourth embodiment of the present invention.
Figure 17:
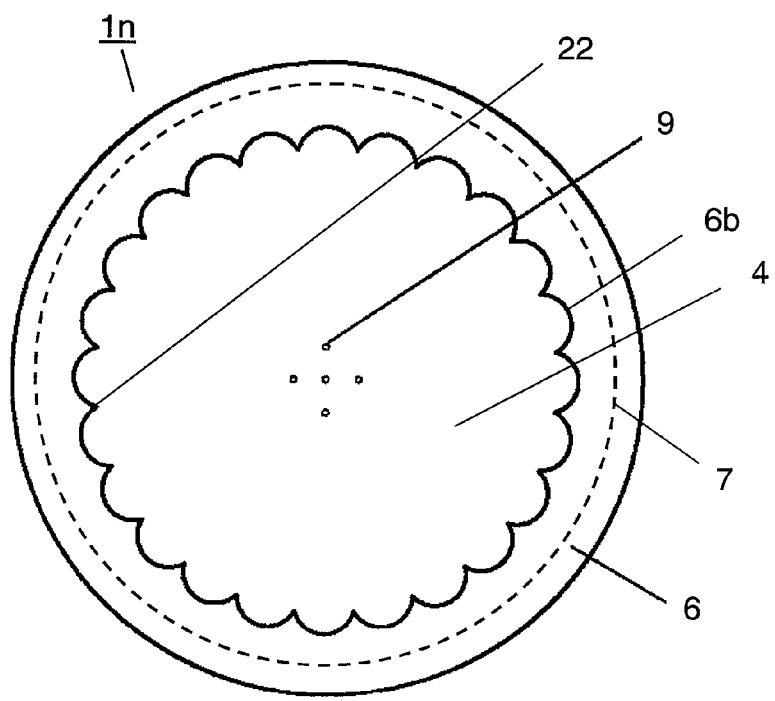
FIG. 17 is an enlarged plan view of an essential part of a cellular electrophysiological measurement device of another aspect of the fourth embodiment of the present invention.
Figure 18:
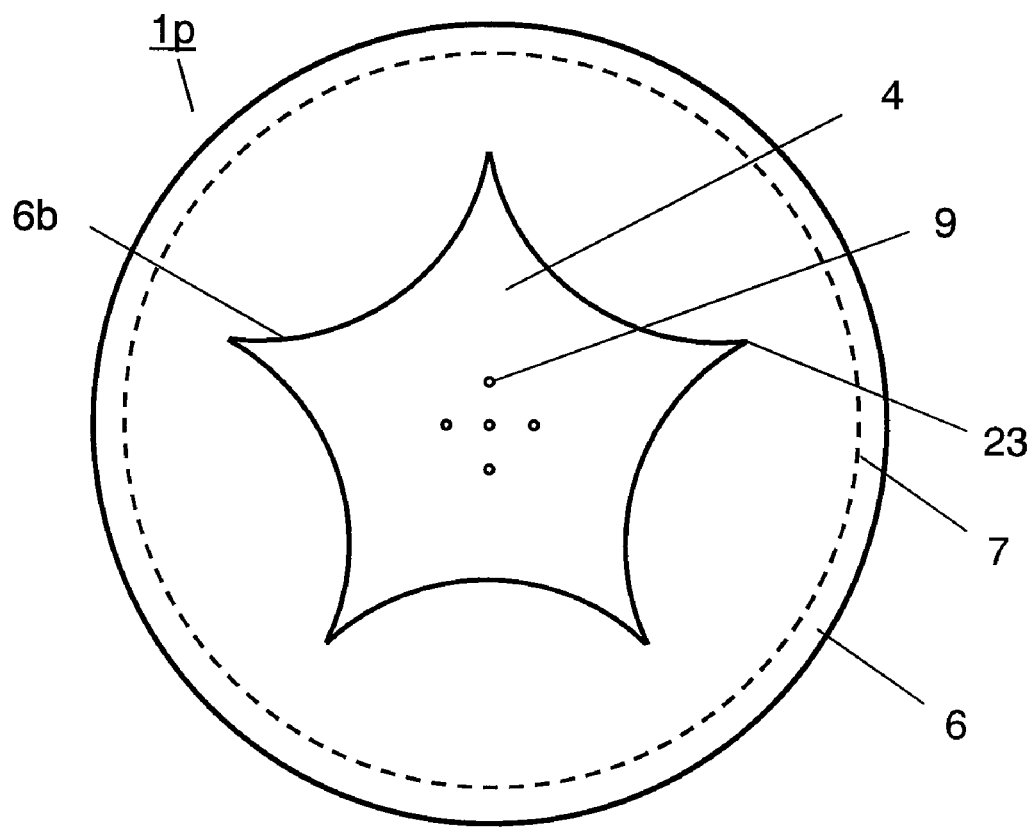
FIG. 18 is an enlarged plan view of an essential part of a cellular electrophysiological measurement device of another aspect of the fourth embodiment of the present invention.
Figure 19:
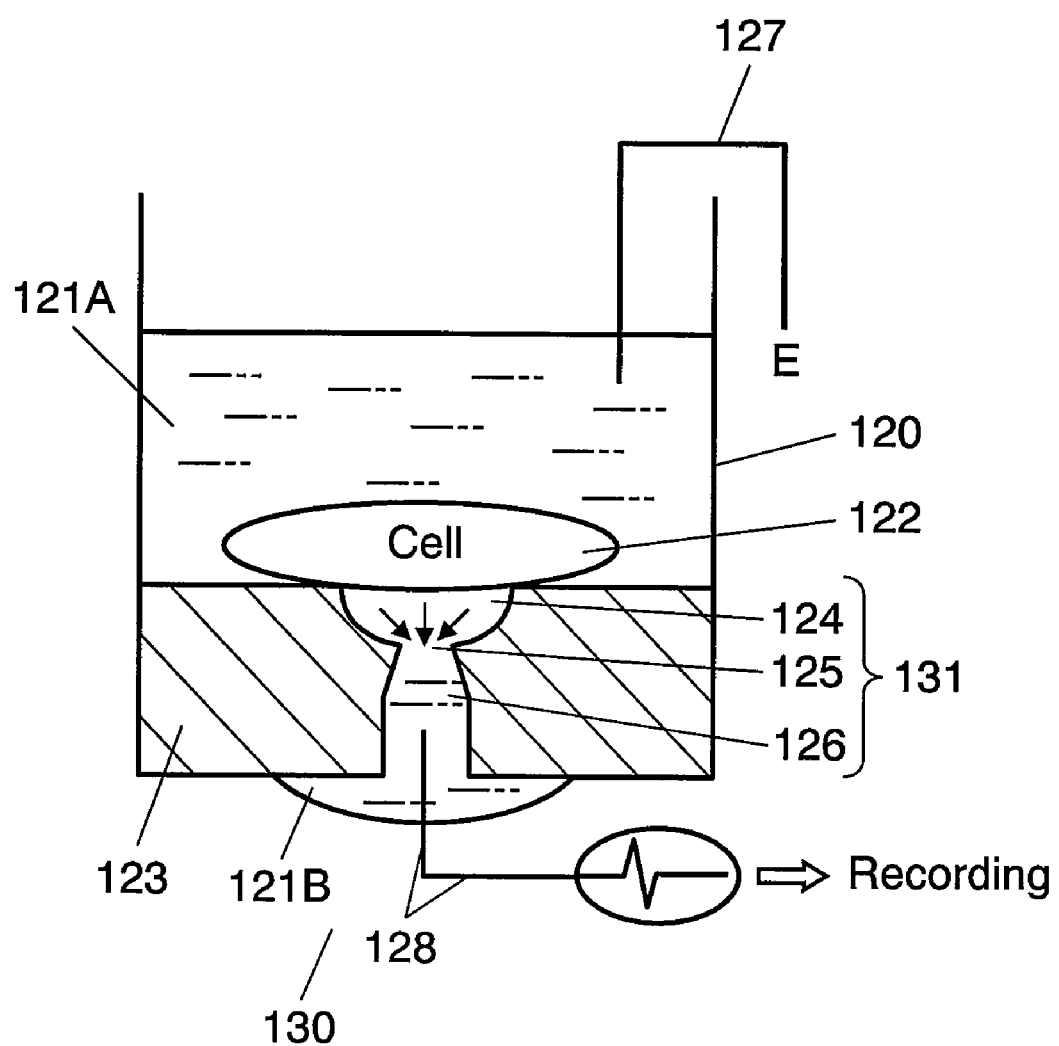
FIG. 19 is a schematic sectional view showing a conventional cellular electrophysiological measurement device.

FIG. 16 is an enlarged plan view of an essential part of the cellular electrophysiological measurement device of the fourth embodiment. FIGS. 17 and 18 are enlarged plan views of essential parts of cellular electrophysiological measurement devices of other aspects of the fourth embodiment.

As shown in FIG. 16, in cellular electrophysiological measurement device 1m (hereinafter, device 1m) of the fourth embodiment, inner wall 6b of frame 6 has a polygonal structure including of three or more straight lines. The polygonal structure makes thin plate 7 less breakable, so that device 1m has an improved strength and hence improved production yield. The structure also makes thin plate 7 more resistant to the suction pressure applied thereto to suck and measure cell 16, so that device 1m can have thin plate 7 that is not easily broken.

As another aspect, FIG. 17 shows cellular electrophysiological measurement device 1n (hereinafter, device 1n). In device 1n, inner wall 6b of frame 6 includes at least one protrusion 22 protruding inwardly. This structure makes thin plate 7 less breakable so as to improve the strength of device 1n. As a result, device 1n can have the same effect as device 1m shown in FIG. 16.

As further another aspect, FIG. 18 shows cellular electrophysiological measurement device 1p (hereinafter, device 1p). In device 1p, inner wall 6b of frame 6 is star-shaped and includes at least one acute recess 23. The recess 23 of the star-shaped structure facilitates the flow of air bubbles (unillustrated) by guiding them along its tip, the air bubbles being formed in measuring solutions 15a and 15b when solutions 15a and 15b are introduced into inner wall 6b. This structure prevents the air bubbles from remaining inside inner wall 6b and also facilitates the flow of measuring solutions 15a and 15b into inner wall 6b. As a result, cell 16 can be measured with improved precision.

Industrial Applicability

As described hereinbefore, the cellular electrophysiological measurement device with improved strength and reduced size and the method for manufacturing the device according to the present invention are useful in such as drug screening to detect a reaction of a cell to a chemical substance.

The invention claimed is:

1. A cellular electrophysiological measurement device comprising:
    a thin plate having a first surface with a depression and a second surface with a through-hole, wherein the through-hole has an opening whose edge is rounded off around an entire perimeter of the opening; and
    a frame in contact with an outer periphery on the second surface of the thin plate, wherein the frame has an inner wall with a protrusion,
    wherein the thin plate has a laminated structure of at least two layers where the first surface is formed of a first material layer and the second surface is formed of a second material layer,
    the through-hole extends through both the first and second material layers, and
    the frame is formed of a third material layer.

2. The cellular electrophysiological measurement device of claim 1,
    wherein the outer periphery of the thin plate is smaller in size than an outer periphery of the frame.

3. The cellular electrophysiological measurement device of claim 1,
    wherein the first material layer is larger in thickness than the second material layer.

4. The cellular electrophysiological measurement device of claim 1,
    wherein the through-hole has an opening whose edge is tapered around an entire perimeter of the opening.

5. The cellular electrophysiological measurement device of claim 1,
    wherein the first material layer and the third material layer are made of silicon, and
    the second material layer is made of silicon dioxide.

6. The cellular electrophysiological measurement device of claim 1,
    wherein the first material layer is rounded off at an upper outer peripheral edge of an outer periphery thereof.

7. The cellular electrophysiological measurement device of claim 1,
    wherein the frame has an inner wall and an outer wall, and the inner wall is rounded off at an inner wall edge, and the outer wall is rounded off at an outer peripheral edge.

8. A method for manufacturing a cellular electrophysiological measurement device which measures a cellular electrophysiological activity, the cellular electrophysiological measurement device including:
    a thin plate having a first surface formed of a first material layer and a second surface formed of a second material layer;
    a depression provided on the first surface of the thin plate;
    a through-hole provided on the second surface of the thin plate, wherein the through-hole extends through both the first and second material layers and has an opening whose edge is rounded off around an entire perimeter of the opening; and a frame in contact with the second surface of the thin plate, wherein the frame has an inner wall with a protrusion, and the method comprising:
- a first-resist-film forming step for forming a first etching resist film having a first resist film opening on a first material layer of a substrate formed of the first material layer, a second material layer, and a third material layer laminated together;
- a depression forming step for forming the depression in the first material layer by introducing a first etching gas from the first resist film opening;
- a first-through-hole forming step for forming a first hole in the first material layer by introducing a second etching gas and a third etching gas from the first resist film opening;
- a first-resist-film removing step for removing the first etching resist film;
- a second-through-hole forming step for forming a second hole in the second material layer by introducing a fourth etching gas;
- a second-resist-film forming step for forming a second etching resist film having a second resist film opening on the third material layer of the substrate; and
- a frame forming step for forming the frame by introducing the second etching gas and the third etching gas from the second resist film opening, wherein the method additionally comprises at least one smoothing step selected from the group consisting of:
- a first smoothing step for smoothing a surface of the substrate by soaking the substrate in an aqueous solution containing abrasive grains and subjecting the substrate to ultrasonic vibration;
- a second smoothing step for smoothing at least one of a surface of an inner wall of the first hole formed in the first material layer and a surface of an inner wall of the second hole formed in the second material layer by melting the at least one of the inner wall of the first hole and the inner wall of the second hole by applying a laser beam from at least one of a side of the first material layer and a side of the third material layer;
- a third smoothing step for smoothing a surface of the substrate by plasma etching using argon gas introduced from a side of the third material layer; and
- a fourth smoothing step for smoothing a surface of the substrate by chemical etching.

9. The method for manufacturing a cellular electrophysiological measurement device of claim 8 further comprising:
- a protective-layer forming step for forming a protective layer, which is made of an electrical insulating material, on a surface of the through-hole from at least one of a side of the first material layer and a side of the third material layer.

10. A method for manufacturing a cellular electrophysiological measurement device which measures a cellular electrophysiological activity, the cellular electrophysiological measurement device including:
- a thin plate having a first surface formed of a first material layer and a second surface formed of a second material layer;
- a depression provided on a first surface of the thin plate;
- a through-hole provided on a second surface of the thin plate, wherein the through-hole extends through both the first and second material layers and has an opening whose edge is rounded off around an entire perimeter of the opening; and a frame in contact with the second surface of the thin plate, wherein the frame has an inner wall with a protrusion, and the method comprising:
- a first-resist-film forming step for forming a first etching resist film having a first resist film opening on a first material layer of a substrate formed of the first material layer, a second material layer, and a third material layer laminated together;
- a depression forming step for forming the depression in the first material layer by introducing a first etching gas from the first resist film opening;
- a second-through-hole forming step for forming a second hole in the second material layer by introducing a fourth etching gas from the first resist film opening;
- a second-resist-film forming step for forming a second etching resist film having a second resist film opening on the third material layer of the substrate; and
- a frame forming step for forming the frame by introducing a second etching gas and a third etching gas from the second resist film opening, wherein the method additionally comprises at least one smoothing step selected from the group consisting of:
- a first smoothing step for smoothing a surface of the substrate by soaking the substrate in an aqueous solution containing abrasive grains and subjecting the substrate to ultrasonic vibration;
- a second smoothing step for smoothing at least one of a surface of an inner wall of the first hole formed in the first material layer and a surface of an inner wall of the second hole formed in the second material layer by melting the at least one of the inner wall of the first hole and the inner wall of the second hole by applying a laser beam from at least one of a side of the first material layer and a side of the third material layer;
- a third smoothing step for smoothing a surface of the substrate by plasma etching using argon gas introduced from a side of the third material layer; and
- a fourth smoothing step for smoothing a surface of the substrate by chemical etching.

11. The method for manufacturing a cellular electrophysiological measurement device of claim 10 further comprising:
- a protective-layer forming step for forming on a surface of the through-hole a protective layer made of an electrical insulating material from a side of the third material layer.

12. The method for manufacturing a cellular electrophysiological measurement device of claim 10 further comprising:
- before the frame forming step, a first rounding-off step for rounding off an inner wall edge at a bottom of the frame and an outer peripheral edge of the frame by dry etching using the first etching gas introduced from the second resist film opening.

13. The method for manufacturing a cellular electrophysiological measurement device of claim 10 further comprising:
- after the second-through-hole forming step, a second rounding-off step for rounding off a top edge of an outer periphery of the frame by dry etching using the first etching gas.

14. A cellular electrophysiological measurement device comprising:
- a thin plate having a first surface formed of a first material layer with a depression and a second surface formed of a second material layer with a through-hole, wherein the through-hole extends through both the first and second material layers and has an opening whose edge is rounded off around an entire perimeter of the opening; and a frame in contact with an outer periphery on the second surface of the thin plate, wherein the frame has an inner wall with a protrusion, wherein the thin plate has a laminated structure of at least two layers.

15. A method for manufacturing a cellular electrophysiological measurement device which measures a cellular electrophysiological activity, the cellular electrophysiological measurement device including:

a thin plate having a first surface formed of a first material layer and a second surface formed of a second material layer;

a depression provided on the first surface of the thin plate;

a through-hole provided on the second surface of the thin plate, wherein the through-hole extends through both the first and second material layers and has an opening whose edge is rounded off around an entire perimeter of the opening; and a frame in contact with the second surface of the thin plate, wherein the frame has an inner wall with a protrusion, and the method comprising:

a first-resist-film forming step for forming a first etching resist film having a first resist film opening on a substrate;

a depression forming step for forming the depression in the substrate by introducing a first etching gas from the first resist film opening;

a first-through-hole forming step for forming a first hole in the substrate by introducing a second etching gas and a third etching gas from the first resist film opening;

a first-resist-film removing step for removing the first etching resist film;

a second-through-hole forming step for forming a second hole in the substrate by introducing a fourth etching gas;

a second-resist-film forming step for forming a second etching resist film having a second resist film opening on the substrate; and a frame forming step for forming the frame by introducing the second etching gas and the third etching gas from the second resist film opening, wherein the method additionally comprises at least one smoothing step selected from the group consisting of:

a first smoothing step for smoothing a surface of the substrate by soaking the substrate in an aqueous solution containing abrasive grains and subjecting the substrate to ultrasonic vibration;

a second smoothing step for smoothing at least one of a surface of an inner wall of the first hole and a surface of an inner wall of the second hole by melting the at least one of the inner wall of the first hole and the inner wall of the second hole by applying a laser beam;

a third smoothing step for smoothing a surface of the substrate by plasma etching; and a fourth smoothing step for smoothing a surface of the substrate by chemical etching.

16. A method for manufacturing a cellular electrophysiological measurement device which measures a cellular electrophysiological activity, the cellular electrophysiological measurement device including:

a thin plate having a first surface formed of a first material layer and a second surface formed of a second material layer;

a depression provided on a first surface of the thin plate;

a through-hole provided on a second surface of the thin plate, wherein the through-hole extends through both the first and second material layers and has an opening whose edge is rounded off around an entire perimeter of the opening; and a frame in contact with the second surface of the thin plate, wherein the frame has an inner wall with a protrusion, and the method comprising:

a first-resist-film forming step for forming a first etching resist film having a first resist film opening on a substrate;

a depression forming step for forming the depression in the substrate by introducing a first etching gas from the first resist film opening;

a second-through-hole forming step for forming a second hole in the substrate by introducing a fourth etching gas from the first resist film opening;

a second-resist-film forming step for forming a second etching resist film having a second resist film opening on the substrate; and a frame forming step for forming the frame by introducing a second etching gas and a third etching gas from the second resist film opening, wherein the method additionally comprises at least one smoothing step selected from the group consisting of:

a first smoothing step for smoothing a surface of the substrate by soaking the substrate in an aqueous solution containing abrasive grains and subjecting the substrate to ultrasonic vibration;

a second smoothing step for smoothing at least one of a surface of an inner wall of the first hole and a surface of an inner wall of the second hole by melting the at least one of the inner wall of the first hole and the inner wall of the second hole by applying a laser beam;

a third smoothing step for smoothing a surface of the substrate by plasma etching using argon gas; and a fourth smoothing step for smoothing a surface of the substrate by chemical etching.

17. A cellular electrophysiological measurement device comprising:

a thin plate having a first surface with a depression and a second surface with a through-hole, wherein the through-hole has an opening whose edge is rounded off around an entire perimeter of the opening; and a frame in contact with an outer periphery on the second surface of the thin plate, wherein the frame has an inner wall of a star-shape with an acute recess, wherein the thin plate has a laminated structure of at least two layers where the first surface is formed of a first material layer, the through-hole extends through both the first and second material layers, and the second surface is formed of a second material layer, and the frame is formed of a third material layer.

* * * * *